(12) United States Patent
Schroeder et al.

(10) Patent No.: US 11,214,564 B2
(45) Date of Patent: Jan. 4, 2022

(54) COMPOUNDS WITH THYMINE SKELETON FOR USE IN MEDICINE

(71) Applicant: TECHNISCHE UNIVERSITÄT DRESDEN, Dresden (DE)

(72) Inventors: Michael Schroeder, Dresden (DE); Yixin Zhang, Dresden (DE); Jörg-Christian Heinrich, Berlin (DE); Joachim Haupt, Bobritzsch-Hilbersdorf (DE); Petra Lennig, Dresden (DE)

(73) Assignee: TECHNISCHE UNIVERSITÄT DRESDEN, Dresden (DE)

( * ) Notice: Subject to any disclaimer, the term of this patent is extended or adjusted under 35 U.S.C. 154(b) by 0 days.

(21) Appl. No.: 17/087,806

(22) Filed: Nov. 3, 2020

(65) Prior Publication Data
US 2021/0130328 A1    May 6, 2021

(30) Foreign Application Priority Data

Nov. 5, 2019   (EP) .................................... 19207030

(51) Int. Cl.
*C07D 403/10*    (2006.01)
*C07D 239/54*    (2006.01)
*A61K 45/06*     (2006.01)

(52) U.S. Cl.
CPC ......... *C07D 403/10* (2013.01); *C07D 239/54* (2013.01); *A61K 45/06* (2013.01)

(58) Field of Classification Search
CPC ...... C07D 401/12; C07D 403/10; A61P 35/00
See application file for complete search history.

(56) References Cited

FOREIGN PATENT DOCUMENTS

| DE | 102008035299 A1 | 2/2010 |
| WO | 2009039127 A1 | 3/2009 |
| WO | 2009039135 A1 | 3/2009 |
| WO | 2009156182 A2 | 12/2009 |
| WO | 2013114339 A1 | 8/2013 |
| WO | 2016016268 A1 | 2/2016 |

OTHER PUBLICATIONS

Hernández, Ana-Isabel et al., "Improving the Selectivity of Acyclic Nucleoside Analogues as Inhibitors of Human Mitochondrial Thymidine Kinase. Replacement of a Triphenylmethoxy Moiety with Substituted Amines and Carboxamides," Bioorganic & Medicinal Chemistry Letters 13, (2003), 3027-3030.
Extended European Search Report for European Patent Application No. 19207030.8, dated Jan. 14, 2020, 7 pp.
Heinrich, Jörg C. et al., "New HSP27 Inhibitors Efficiently Suppress Drug Resistance development in Cancer Cells," Impact Journals, Oncotarget, vol. 7, No. 42 pp. 68156-68169, 2016.
Hildebrand, Catherine et al., "Structure-Activity Relationships of $N^2$-Substituted Guanines as Inhibitors of HSV1 and HSV2 Thymidine Kinases," Journal of Medical Chemistry, 1990, 33, pp. 203-206.
Jakob, Ursula et al., "Small Heat Shock Proteins are Molecular Chaperones*," The Journal of Biological Chemistry, vol. 268, No. 3, Issue Jan. 25, 1993, pp. 1517-1520.

*Primary Examiner* — Rei Tsang Shiao
(74) *Attorney, Agent, or Firm* — Heslin Rothenberg Farley & Mesiti P.C.

(57) ABSTRACT

The present invention relates to novel compounds as new chemical entities with thymine skeleton, these compounds for use as in medicine, especially in the treatment of carcinoma, HSP27-associated diseases and cystic fibrosis; and a pharmaceutical product containing at least one of these compounds. Finally, a method of production of that novel compounds is presented.
General formula of these compounds is formula (I):

as further defined in claim 1.

9 Claims, 2 Drawing Sheets

COMPOUNDS WITH THYMINE SKELETON FOR USE IN MEDICINE

CROSS REFERENCE TO RELATED APPLICATIONS

This application claims priority to European Application No. 19 207 030.8, filed on Nov. 5, 2019, the entire contents of which are hereby incorporated herein by reference.

BACKGROUND OF THE INVENTION

The present invention relates to novel compounds as new chemical entities with thymine skeleton. These compounds are applicable for various diseases and can be use as medicinal products.

Thymine derivatives play an important role in the pharmaceutical field. Physiologically it is active in treatment of various diseases.

For example WO2009/039127A1 discloses thymine derivatives for treating hepatitis C.

Various thymine structures were tested for interaction with chaperone proteins, which include the heat shock proteins like HSP27, by Heinrich et al. (2016) and which are also involved in many diseases. Chaperones play a central role in the folding of proteins. In cancer cells, for example, they are regularly overexpressed.

Hernández et al. (2003) investigated thymine derivatives against target thymidine kinase (TK-2) and herpes simplex virus type 1 thymidine kinase.

Structurally different guanine derivatives were tested by Hildebrand et al. (1990) for inhibition of HSV-1 and HSV-2 thymidine kinase.

WO2009156182A2 describes uracil derivatives.

WO2016016268A1 describe thymine and quinazolinedione derivatives.

As one example, WO2013114339A1 discloses a synergistic effect of a nucleotide inhibitor for inhibiting the expression of HSP27 in conjunction with an inhibitor of EGFR (epidermal growth factor receptor) protein activity. However, one disadvantage in the use of nucleotide-based inhibitors is their excess of negative charges and the associated high polarity of the active ingredient molecules, significantly minimizing bioavailability. In addition, nucleotide-based inhibitors are chemically unstable.

A major disadvantage of such nucleotide-based inhibitors as therapeutics is that they must be administered parenterally. A further disadvantage is that current nucleotide-based therapeutic candidates demonstrate only low efficacy. In addition, short nucleotide-based inhibitors have the disadvantage of potentially inducing immunogenicity, as well as acting indirectly on non-transfected cells e.g. by secretion from the target cell, and thus inducing a strong immune response in the organism. From the pharma economic perspective, nucleotide-based inhibitors are much more costly to produce than small molecule drugs.

The following example illustrates the continuous need for improved pharmaceuticals very well.

DE102008035299A1 describes a method according to which the low-molecular-weight organic compound (E)-5-(2-bromovinyl)-2'-deoxyuridine (BVDU) interacts directly with a chaperone HSP27. However, at an increased administered dose, BVDU proved disadvantageous for patients with low body weight.

There is a constant need for pharmaceutically active new chemical entities, that can be used to treat different illnesses.

BRIEF SUMMARY OF THE INVENTION

The problem that will be solved by the invention is the provision of new chemical entities, especially for pharmaceutical use. Different illnesses should be treatable with that chemical entity. Toxicity to healthy cells should be low. Furthermore, pharmaceutical application of the entities should be easy and comfortable. The molecule itself should be easy to be prepared. These compounds should be stable, especially in the form of a pharmaceutical product, i.e. in a pharmaceutical formulation. In addition, the compounds of this invention should be qualified for treatment of carcinoma or cystic fibrosis.

DETAILED DESCRIPTION OF THE INVENTION

Figure 1A:
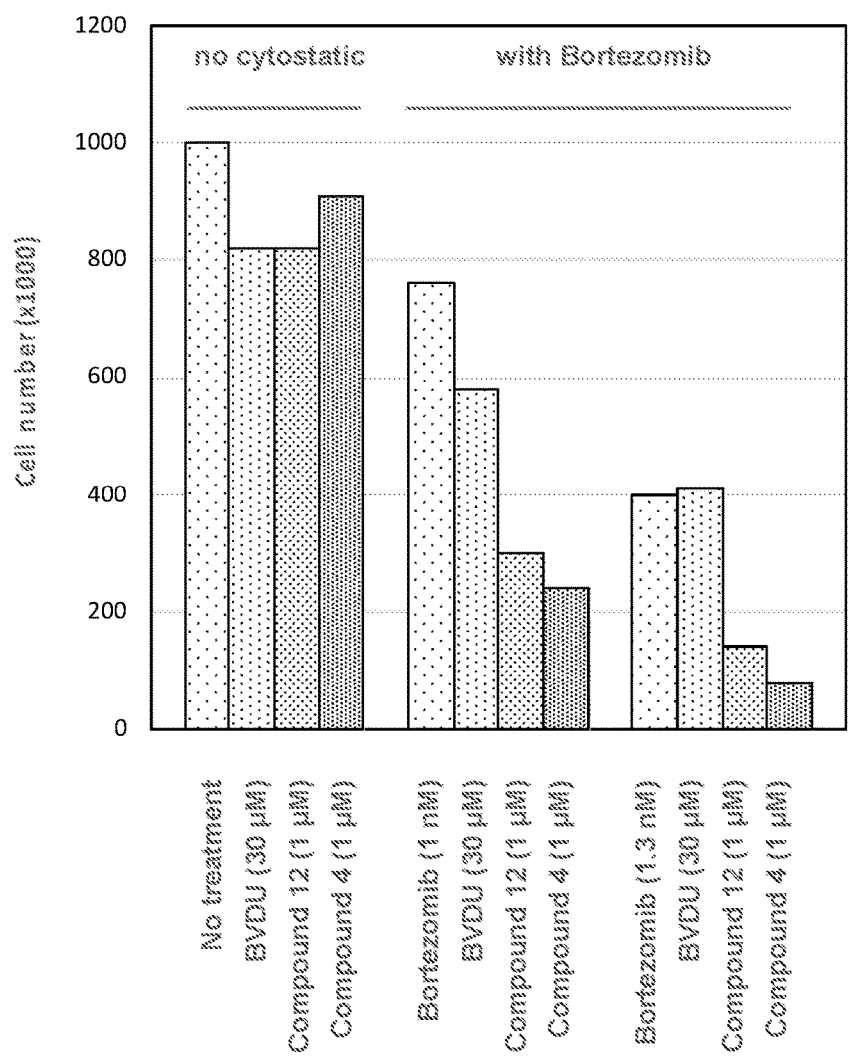
FIGS. 1a and 1b show the results of a chemoresistance assay with two different cell lines for a known cytotoxic and compounds according to the invention (test compounds).

The problem is solved by the invention of independent claims and specified through the dependent claims.

Subject of the invention is a compound according to general formula (I), its salts and prodrugs:

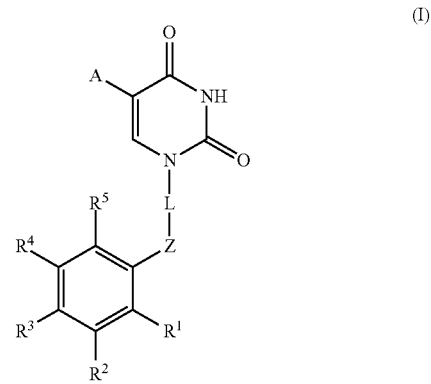

whereas
substituent A is —H, -Hal, -Me or —$CF_3$,
linker L is
a para- or meta-linked phenyl or benzyl group, both substituted or unsubstituted, whereas the $CH_2$ of the benzyl group is arranged in a direction, that it binds to the nitrogen in general formula (I), and
whereas Z is selected from:

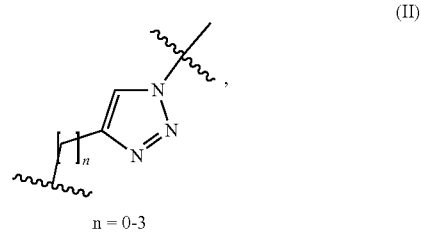

n = 0-3

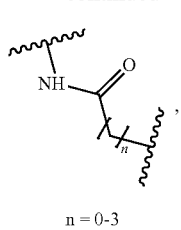

(III)

n = 0-3

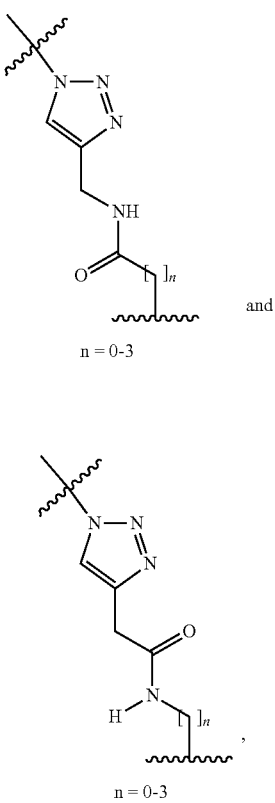

(IV)

n = 0-3 and (V)

n = 0-3 whereas the nitrogen in formulas (II), (III), (IV) and (V) binds to L (i.e. the group in formulas (II), (III), (IV) and (V) is arranged in a direction, that the nitrogen binds to L, consequently, in this arrangement the carbon (and the amide-nitrogen in formula (V), respectively) binds to the C6-aromat in formula (I)), and substituents $R^1$, $R^3$, $R^4$ and $R^5$ are independently selected from —H, -Hal, —$CF_3$, -Me, —OMe, —$OCF_3$ and —$O^iPr$ (isopropyloxy), OEt and substituent $R^2$ is selected from substituted phenyl, unsubstituted phenyl, —H, -Hal, —$CF_3$, -Me, —OMe, —$OCF_3$, —$O^iPr$ and OEt.

"~~" within formulas indicates a bond to another formula or moiety, e.g. the bond of the triazole-nitrogen to L and.

According to the invention, in L the named arrangement of the group $CH_2$ of the benzyl group is arranged in a direction, that it binds to the nitrogen in general formula (I), i.e. it binds to the uracil moiety.

It is also comprised that L can be both substituted and unsubstituted, especially the aromatic ring but also at the $CH_2$-hinge. The same applies for group Z, e.g. the triazole moiety or the $CH_2$-hinge can be substituted or unsubstituted.

The compound according to the invention is a typical low-molecular weight organic compound.

"Substituted" in the meaning of the invention means that at least one and maximum 5, preferred 1 to 3, hydrogen atoms at different and/or the same carbon atoms are substituted by common "small" substituents, for example Halogen, alkoxy with maximum 7 carbon atoms or alkyl with maximum 7 carbon atoms both with cyclic or noncyclic alkyl, $CF_3$, $OCF_3$, etc.

"Para- or meta-linked phenyl or benzyl" according to the invention means that either both bonds to these aromatics occupy the opposite ends of the aromatic ring (para) or the neighbour positions with one position in between (meta).

As low-molecular-weight organic compounds the compounds according to the invention have the advantage over large molecules (e.g. nucleotide-based inhibitors such as antisense oligonucleotides or RNA oligonucleotides) that they are substantially easier to handle and more stable under physiological conditions. They are cell-penetrating and therefore easier to administer into the cell or an organism.

One advantage is that these compounds according to the invention are new and can be used to treat carcinoma, cystic fibrosis (mucoviscidosis) and other HSP27-associated diseases.

Advantageously, the compounds according to the invention inhibits the HSP27 protein (generally named as "activity against HSP27").

One advantage of these compounds consists in the fact that they have a higher activity than currently known compounds regarding the inhibition of HSP27. Especially, it is higher compared with BVDU (brivudine).

Advantageously, the compounds of the invention reduce the development of resistances in chemotherapy, radiotherapy and cancer immunotherapy, in particular in cytostatic treatment, or at least significantly delays those.

Preferred Embodiments

In a preferred embodiment of the invention linker L is substituted at the aromatic ring with alkyl, methoxy and/or halogen, in particular with alkyl and/or methoxy. More preferably, it is substituted with only one substituent (in addition to the two links to N and Z in formula (I)).

In a preferred embodiment of the invention, A in formula (I) is selected from H, Hal, Me. Hal especially is F and Cl.

Preferably, n in Formulas (II), (III), (IV) and (V) is 0-2, more preferably 0-1. More preferably it is 1. Especially in formula (III) 1 is preferred.

In a preferred embodiment of the invention Z is selected from formulas (II), (IV) and (V).

In a preferred embodiment of the invention the aromatic ring in formula (I) is substituted (in addition to Z). More preferably it is disubstituted (in addition to Z).

In a preferred embodiment of the invention the aromatic ring in formula (I) is a biphenyl-group (with the resulting arrangement which can be called "meta-biphenyl"), i.e. in formula (I) $R^2$ is selected from substituted and unsubstituted phenyl. In this case most of the compounds have a structure according to formula (VI) with the same definitions as in formula (I):

(VI)

with R6 to R10 independently selected as defined for the substituents $R^1$, $R^3$, $R^4$ and $R^5$.

In a preferred variant of the above named embodiment, in formula (VI) the first ring is unsubstituted (i.e. $R^1$, $R^3$, $R^4$ and $R^5$ are all hydrogen).

Most preferably, the above named disubstitution relates to this terminal phenyl (i.e. two of the substitutents $R^6$-$R^{10}$ are not hydrogen and the substituents $R^1$, $R^3$, $R^4$ and $R^5$ are all hydrogen.

In another preferred embodiment of the invention, in formula (I) $R^1$ and $R^5$ are both hydrogen, more preferably also $R^3$ and $R^4$ are hydrogen. In a variant of this embodiment, where $R^2$ is phenyl (i.e. as in formula (VI)), $R^6$ and $R^{10}$ both preferably are hydrogen or $R^7$, $R^9$ and $R^{10}$ are all hydrogen.

In a preferred embodiment of the invention $R^2$ is substituted phenyl according to formula (VI) wherein $R^6$, $R^9$ and $R^{10}$ are hydrogen. Especially preferred in this case is that $R^1$, $R^3$, $R^4$ and $R^5$ are as hydrogen.

In a preferred embodiment of the invention the compound according to formula (I) is selected from the following molecules:

6
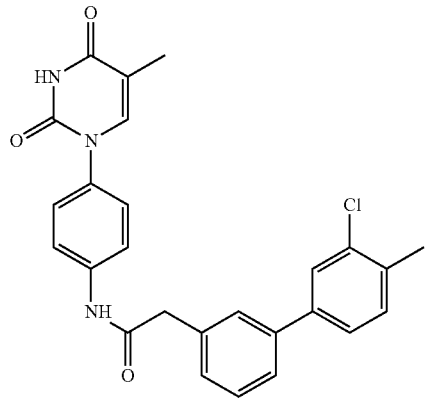
10
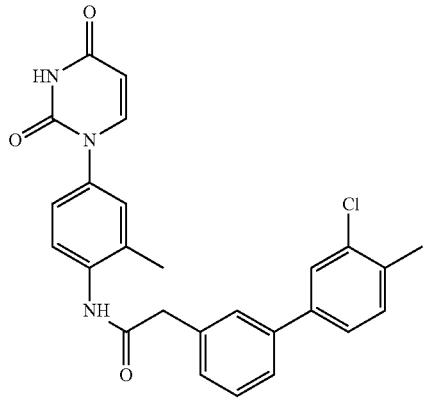
7
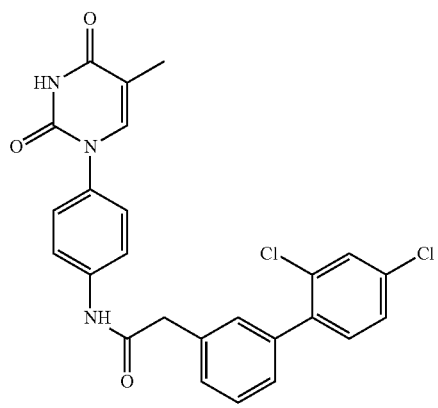
11
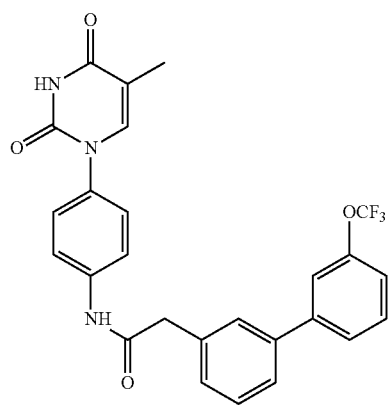
8
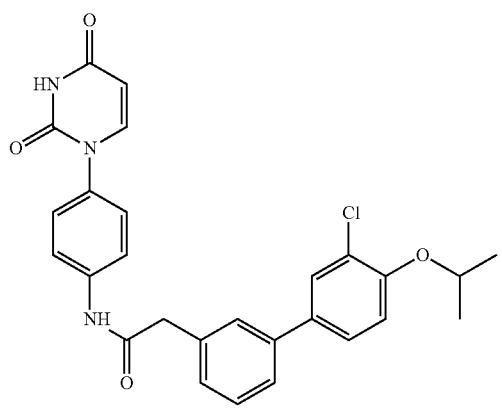
12
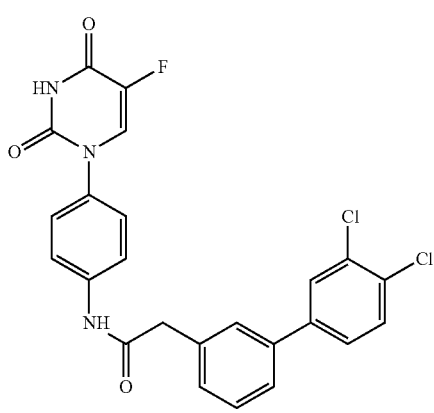
9
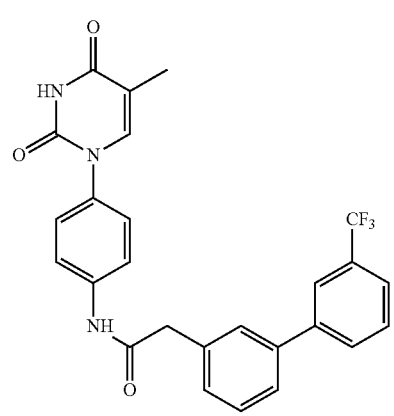
13
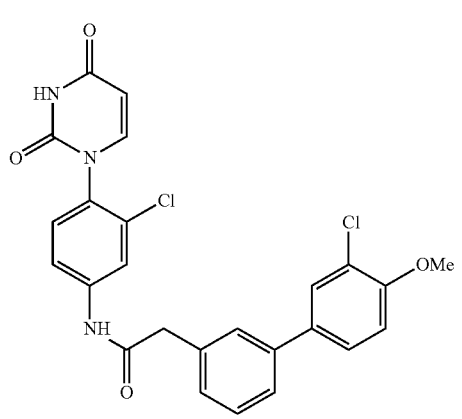

14
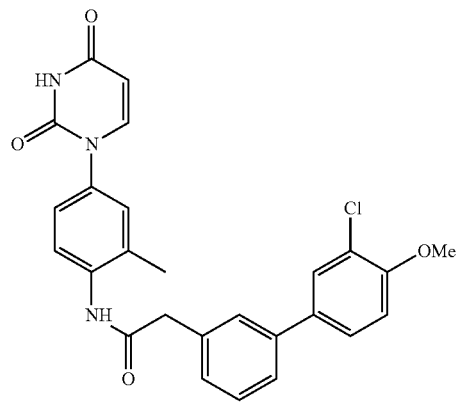
15
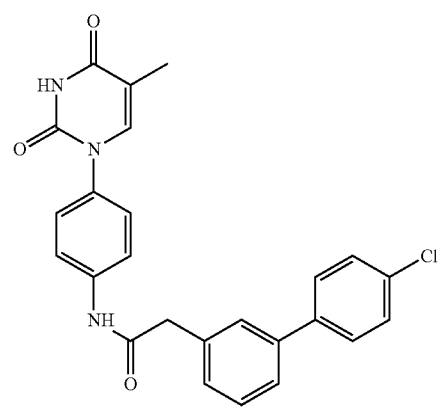
16
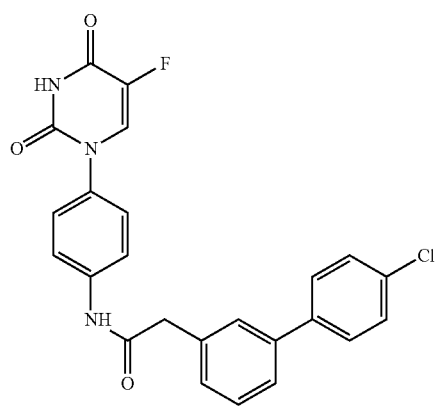
17
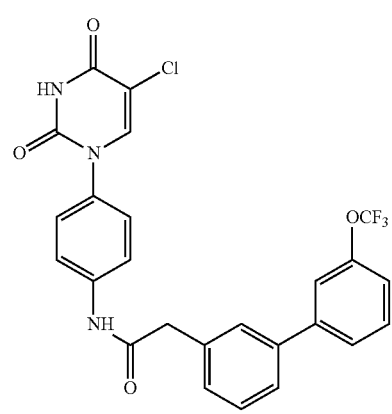
18
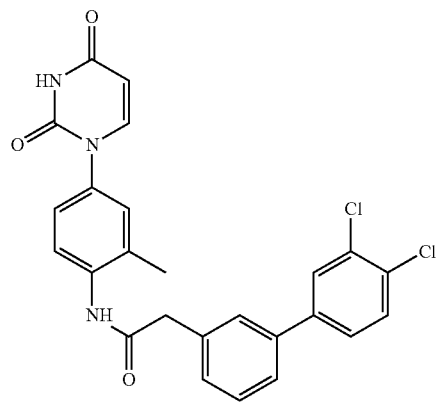
19
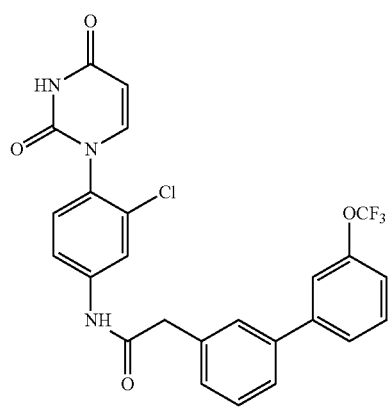
20
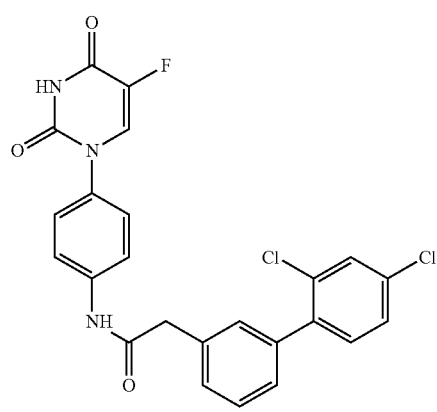
21
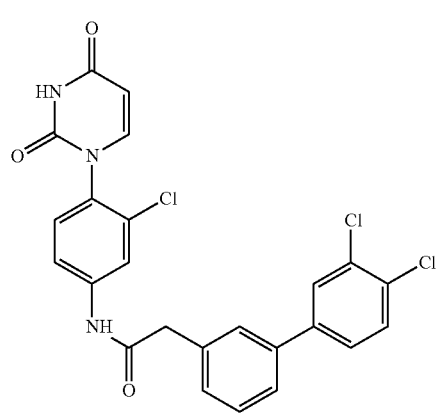

22
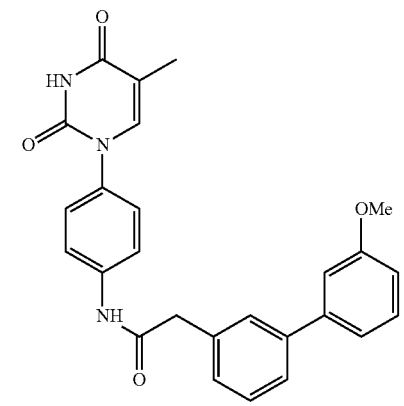
23
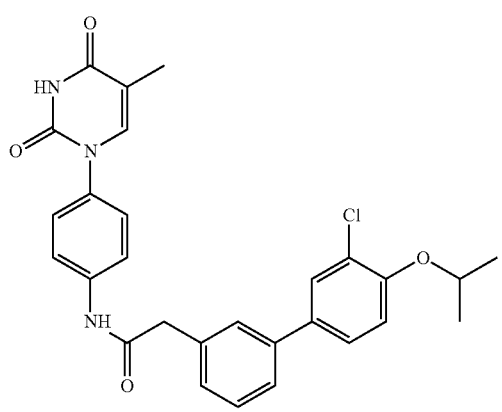
24
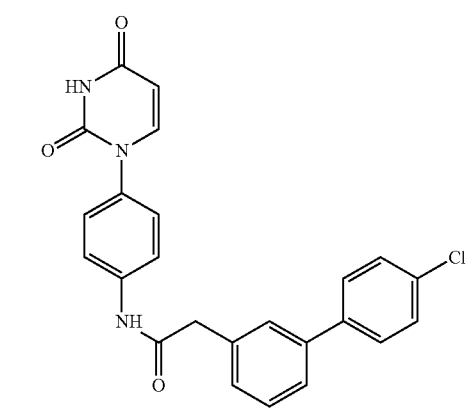
25
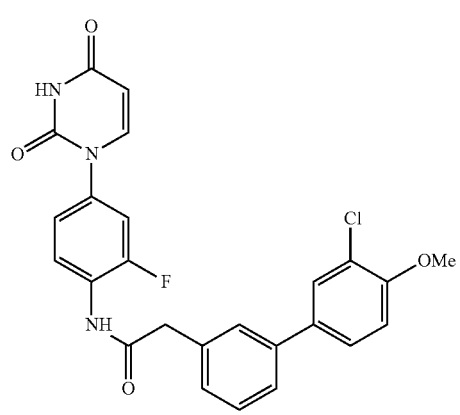
26
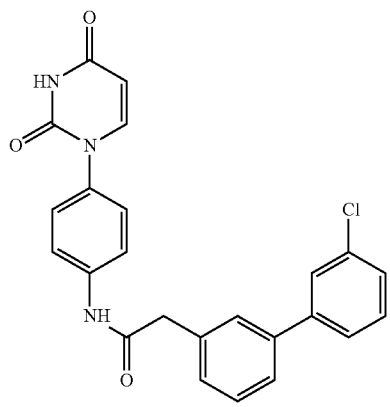
27
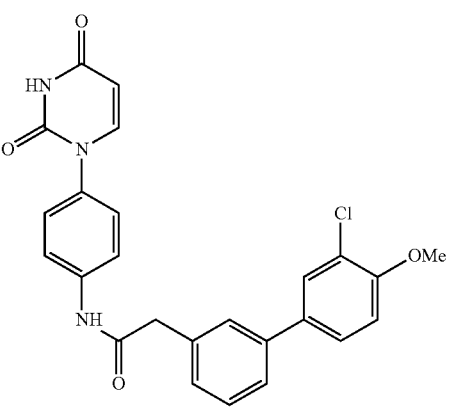
28
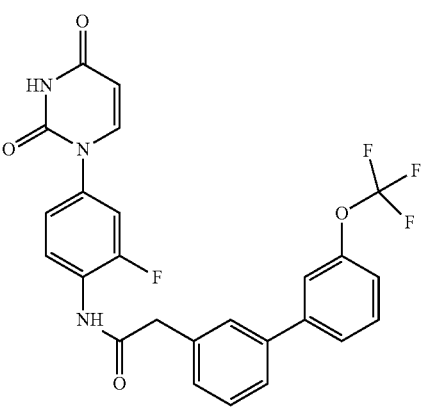
29
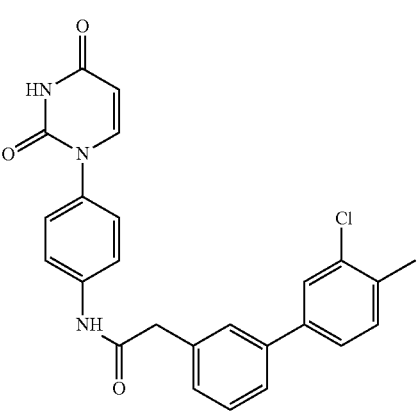

30
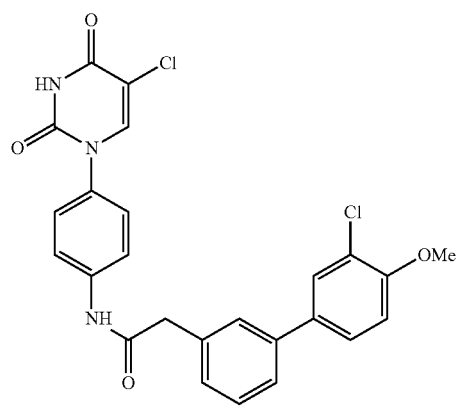
31
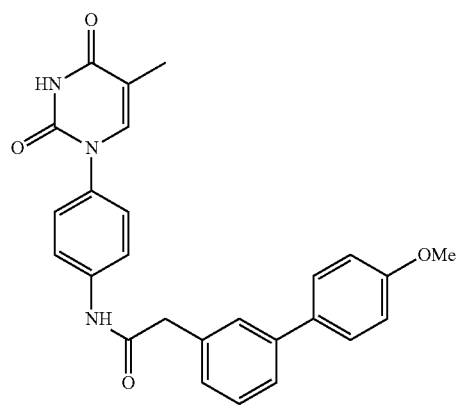
32
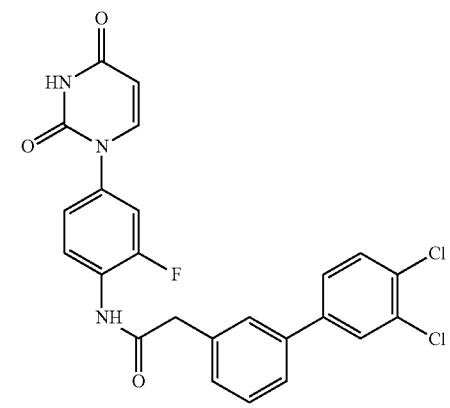
33
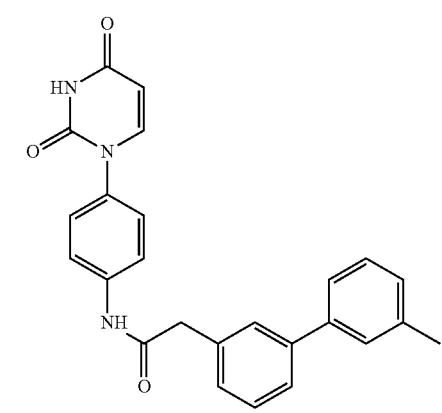
34
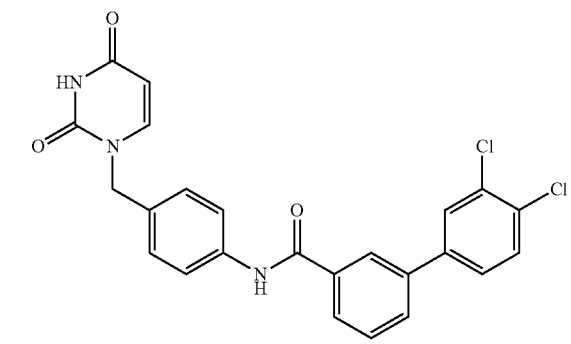
35
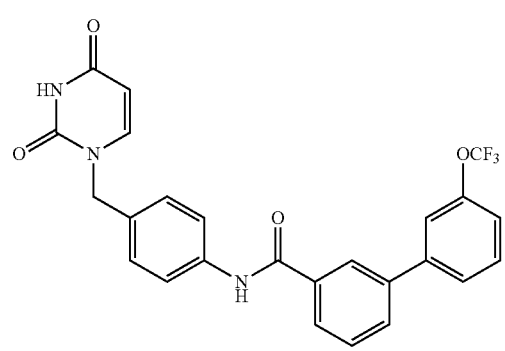
36
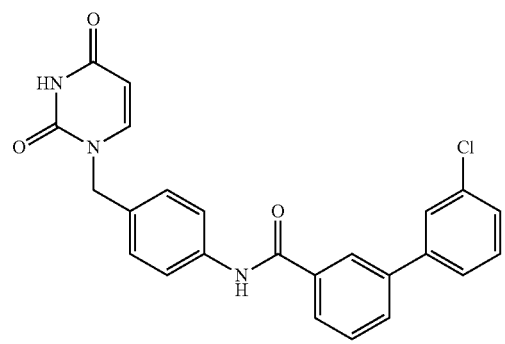
37
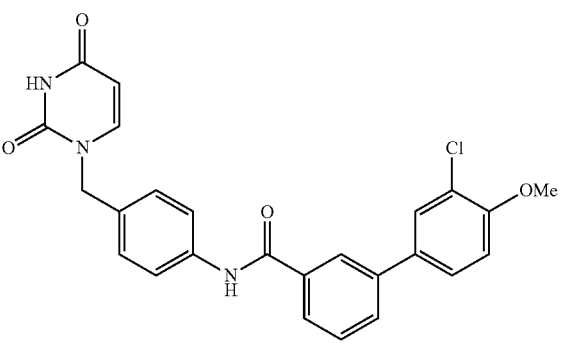

38
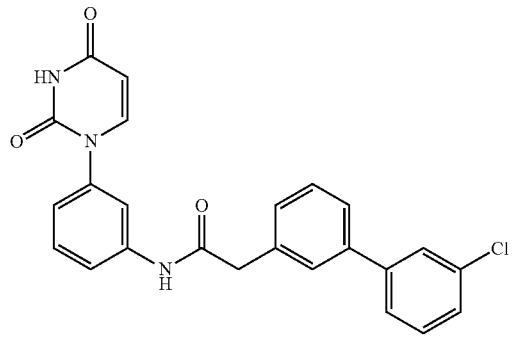
39
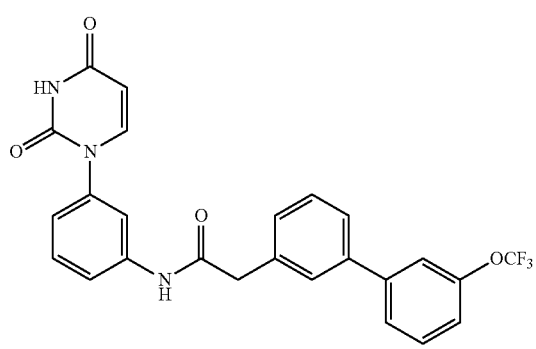
40
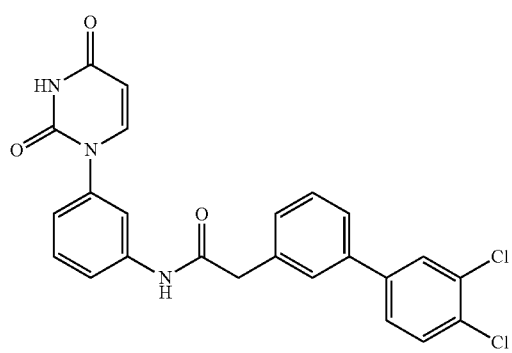
41
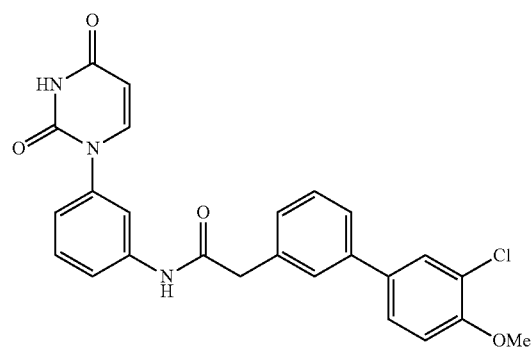
42
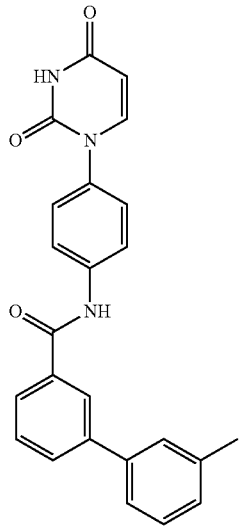
43
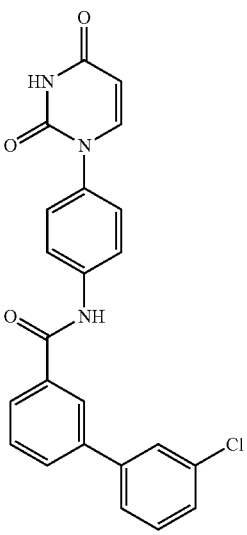
44
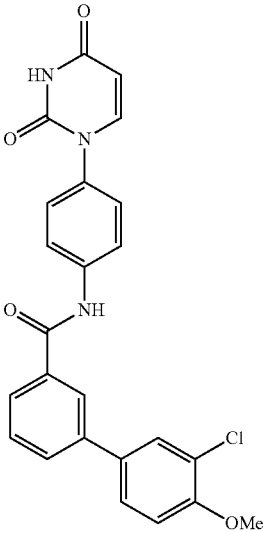

45
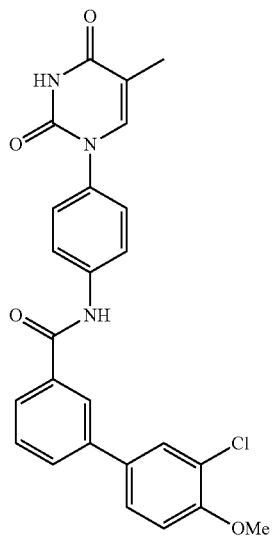
46
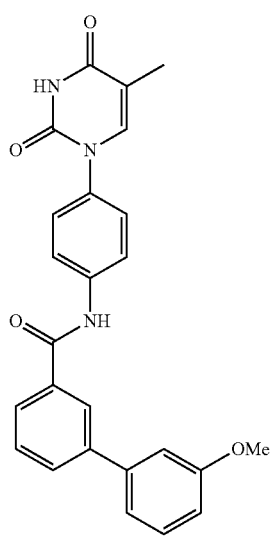
47
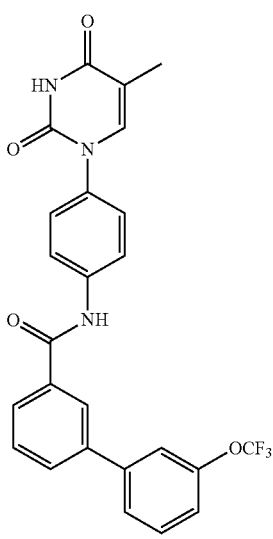
48
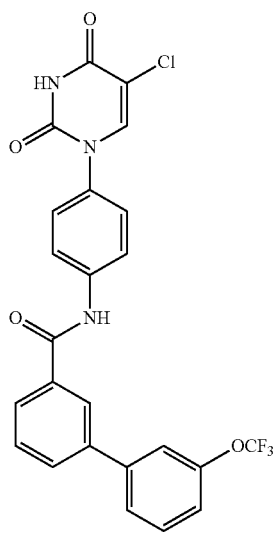
49
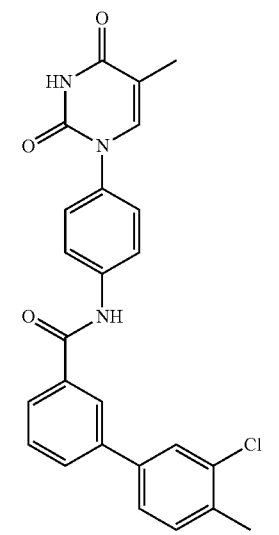
50
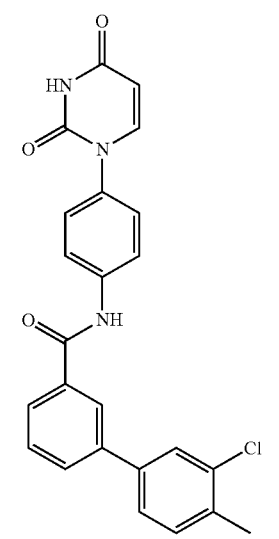

51
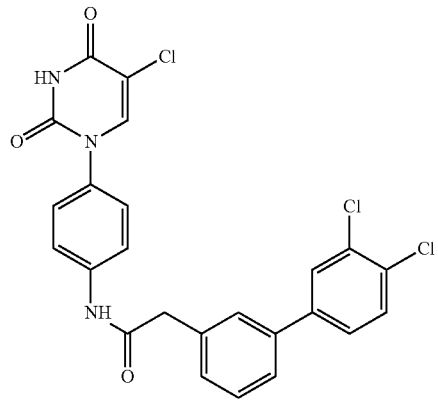
52
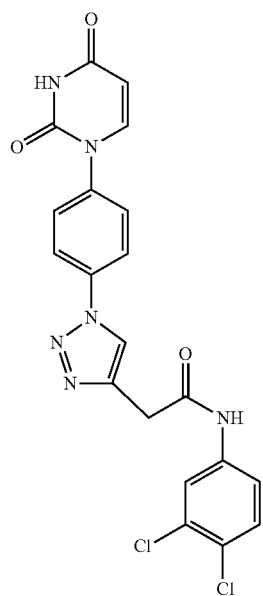
53
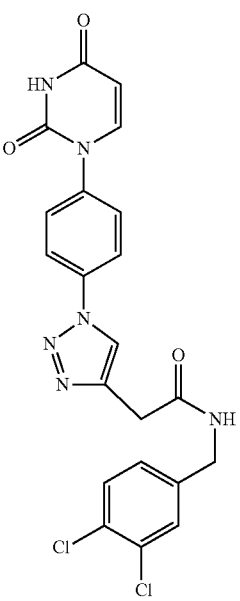
54
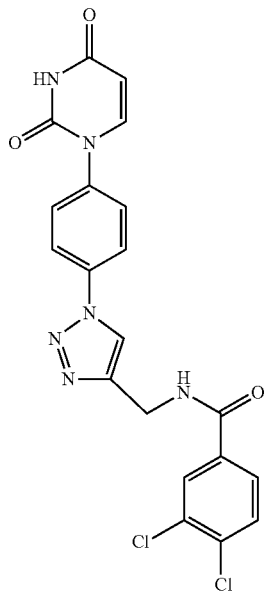
55
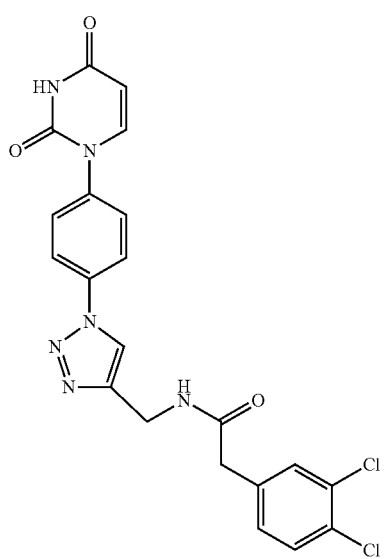

-continued

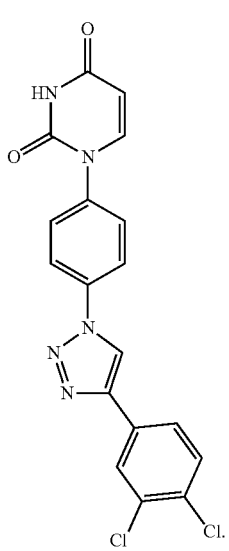

56

The compound according to the invention also comprises its salts, in particular pharmaceutically acceptable salts, and its enantiomers, diastereomers, tautomers, solvates and prodrugs. All these is reflected by the term "its salts and prodrugs". In the rest of the description "its salts and prodrugs" is omitted or indicated via "( . . . )". Nevertheless, it is comprised by "compound" through the whole invention.

Prodrug of a compound is a substance that through metabolic processes (e.g. hydrolysis, enzymatic cleavage etc.) forms this compound. For example, the prodrug can be an ester and the compound after metabolic process (here ester cleavage) is the hydroxy compound, or an amide as prodrug of an amine.

Another subject of the invention is the above named compound for use as in medicine, i.e. as a pharmaceutical. Especially this is the above named compound for use (as pharmaceutical) in the treatment of carcinoma, HSP27-associated diseases and cystic fibrosis (mucoviscidosis). Subject is also the use of this compound as a pharmaceutical, especially in the treatment of the above named diseases.

HSP27-associated diseases are diseases in which HSP27 is overactive, i.e. in which the abnormal high activity leads to suffering of a patient. HSPs have been known for a long time as being able to prevent protein aggregation by binding polypeptide clients destabilized during cellular stress, such as heat shock. HSP27 (HSPB1) is an ATP-independent molecular chaperone that belongs to the group of small HSPs (sHSPs) characterized by a common alpha-crystallin domain in their C-terminus. sHSPs have been described to have a great number of crucial roles in normal unstressed cells, as well as in pathological cells where they are expressed at high levels. These proteins are now considered to be important therapeutic targets, particularly in cancer pathologies. HSP27 is involved in the generation of two large groups of diseases; congenital diseases, due to gene mutations, and degenerative diseases, such as neurodegenerative disorders, cardiovascular pathologies and many forms of advanced cancer and metastasis.

Cancer and Metastasis:

HSP27 is upregulated in many cancer types, including non-small cell lung cancer (NSCLC), breast cancer, ovarian cancer, hepatocellular carcinoma, colon carcinoma, stomach cancer, head and neck cancer, renal cancer, prostate cancer, brain cancer, B.cell lymphoma, multiple myeloma, and others. In these cancers aberrant HSP27 expression correlates with aggressivity of tumor growth, metastasis, as well as therapy resistance.

Congenital Diseases:
Charcot-Marie-Tooth disease type 2, distal hereditary motor neuropathy
Myotonic dystrophy, different forms neuropathology; cardiac and skeletal muscle
Motor neuropathy: cardiac and skeletal muscle
Cataract; cye lens
Dilated cardiomyopathy; cardiac muscle
Pemphigus vulgaris; mucosa and skin
Hence, HSP27-associated diseases in the meaning of this invention are cancer, especially the above named forms, and the above named list of congenital diseases.

The invention also comprises a method for the treatment of patients suffering from one of the above named diseases by administration of an effective dose of the compound according to the invention, in particular administration of the above named pharmaceutical product.

Also a subject of the invention is the use of the compound according to the invention for preparing a medicinal product, preferably for the treatment of the above named diseases.

In a preferred embodiment of the compound ( . . . ) according to the invention for use . . . , it is intended for use (as a pharmaceutical) in the treatment of carcinoma in combination with a chemotherapy, radiotherapy and/or cancer immunotherapy, wherein advantageously the development of resistance to the treatment methods (i.e. ability of a tumour or tumour cells to resist the treatment method employed) is reduced, in particular suppressed.

Especially, in this treatment
the compound ( . . . ) is applied already before start of the chemotherapy, radiotherapy and/or cancer immunotherapy, and
administration of the compound ( . . . ) is continued during these therapies to suppress development of resistances.

Preferably, the administration of the compound ( . . . ) is started 15 min to 4 hours before the start of the chemotherapy, radiotherapy and/or cancer immunotherapy.

In a preferred embodiment of the method for the treatment of carcinoma, HSP27-associated diseases and cystic fibrosis (mucoviscidosis), the compound is administered orally or rectally in an amount of 0.1 to 30 mg/kg body weight per day, in particular 0.5 to 15, in doses of each 0.1 to 500 μmol, in particular 0.5 to 200 μmol, especially 1 to 50 μmol/kg body weight per day.

Another subject of the invention is a pharmaceutical product containing at least one compound according to the invention. This pharmaceutical product can be administered orally in the form of tablets, capsules, liquids or syrup or rectally in the form of suppositories or via injection. The pharmaceutical product normally contains further carriers and additives.

Preferably, the pharmaceutical product of the invention additionally comprises at least one further active ingredient, preferably selected from cancerostatic agents, alkylating agents, inhibitors of DNA replication, inhibitors of DNA transcription and angionesis inhibitors.

For the above named use of the compound according to the invention in the treatment of carcinoma in combination with a chemotherapy, radiotherapy and/or cancer immunotherapy, such a further active ingredient that acts in the chemotherapy is preferably selected from alkylating agents, anthracyclines, cytosketal disruptors, taxanes, epothilones, histone deacytalse inhibitors, inhibitors of topoisomerases (in particular of topoisomerase I or II), kinase inhibitors, nucleotide analogs and precursor analogs, peptide antibiotics, platinum-based agents, retionoids, vinca alkaloids and derivatives. And the further active ingredient that acts in the cancer immunotherapy is preferably selected from antibodies, antibody fragments, aptamers and small interfering nucleic acids (like siRNA and shRNA).

Another subject of the invention is a method for the production of the compound according to the invention, comprising:
(i) coupling of a compound X with a compound Y
  whereas X comprises a terminal —$NH_2$ (amine) group and Y comprises a terminal —COOH (acid) group, to build up the amide-moiety in Z in formula (I) via amine-acid coupling,
  whereas Z is preferably selected from formulas (III), (IV) and (V), or whereas X comprises a terminal —$N_3$ (azide) group and Y comprises a terminal alkine-group (—CCH), to build up the triazole-moiety in Z in formula (I) via click-chemistry, whereas Z is preferably selected from formulas (II), (IV) and (V).

The mentioned coupling via click chemistry (i.e. where X comprises a terminal —$N_3$ group and Y comprises a terminal alkine-group (—CCH)) can also include the previous step of generating the terminal —N group by known methods, such as from a terminal —$NH_2$ group or from common terminal-leaving groups such as —Br, —I etc. As already known, for the azide-alkine-coupling (called click-chemistry) a common catalyst such as $CuSO_4$ can be used. The mentioned amine-acid-coupling, according to known state-of-the-art knowledge, can be performed e.g. with activating agents, such as PyBOP, EDC, CDI, DCC, HOAt, HOBt, HATU, TOTU, TBTU or combinations thereof, and optionally an additional base, such as TEA, DIPEA or N-methylmorpholin in an appropriate inert solvent, for example a hydrocarbon or a chlorinate hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, or an ester such as ethyl acetate or ethyl butanoate or an amide such as N,N-dimethylformamide or N,N-dimethylacetamide or N-methyl-pyridone or in a mixture of solvents. The reaction temperature in this case is generally from –20° C. to 100° C., preferably from 0° C. to 25° C. The reaction time is generally from 15 min to 6 days, preferably from 15 min to 16 h, depending on the composition of the mixture and the chosen temperature range.

Abbreviations: PyBOP (Benzotriazole-1-yl-oxytripyrrolidinophosphonium-hexafluorophosphate), EDC (1-Ethyl-3-(3-dimethylaminopropyl)carbodiimide), CDI (Carbonyldiimidazole), DCC (Dicyclohexylcarbodiimide), HOAt (1-Hydroxy-7-azabenzotriazole), HOBt (1-Hydroxybenzotriazole), HATU (Hexafluorophosphate-Azabenzotriazole-Tetramethyl-Uronium), TOTU (O-[(Ethoxycarbonyl)cyanomethyleneamino]-N,N,N',N'-tetramethyluronium tetrafluoroborate), TBTU (2-(1H-Benzotriazole-1-yl)-1,1,3,3-tetramethylaminium tetrafluoroborate), TEA (Triethylamine), DIPEA (Diisopropylethylamine).

As known, the introduction of formula (b) for example can happen directly or in subsequent steps. "Directly", in this case, means that already the compounds X or Y in the coupling (i) comprise formula (b). "In subsequent steps", in this case, means for example that after coupling (i) of X and Y further modification of the resulting compound is needed to include formula (b) in that compound. Another example for "in subsequent steps" is the coupling of the azide with an N-protected alkine, e.g. Alkine-NHBoc that is deprotected after coupling and reacted with a carboxylic acid that bears, for example, the residue shown in formula (b).

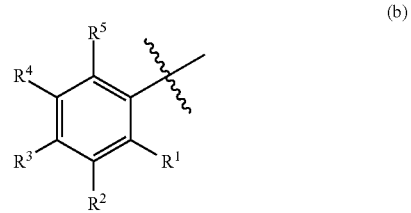

(b)

In a preferred embodiment of the method for the production of the compound according to the invention, the method comprises the steps
(ii) coupling of a compound of formula

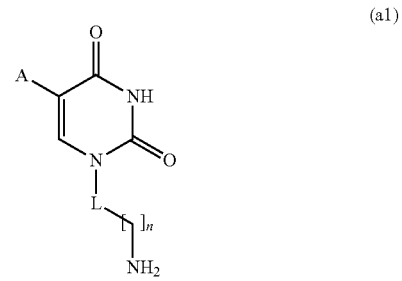

(a1)

with a carboxylic acid to build up the amide-moiety in Z in formula (I) via amine-acid coupling, whereas Z is preferably selected from formulas (III) and (IV),
or of formula

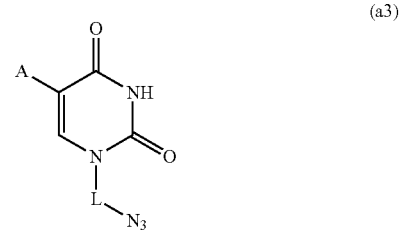

(a3)

with an alkine-compound to build up the triazole-moiety in Z in formula (I) via click-chemistry, whereas Z is preferably selected from formulas (II), (IV) and (V),
  whereas n=0-3 and
(iii) introducing formula (b) either in coupling with the carboxylic acid or with the alkine-compound, directly, or in subsequent steps,
  to yield the compound according to the invention of formula (I) with all definitions made for the residues A, L, $R^1$-$R^5$ and Z above.

In this embodiment, consequently (ii) represents (i).

Scheme A shows a general synthesis route for those compounds bearing an amide group as Z in formula (I).

Scheme B shows another synthesis route for compounds bearing a triazole group within Z in formula (I).

Table 1 shows HPLC-parameters used in purification of the final compounds.

Tables 2 to 4 show various building blocks prepared.

Table 5 shows various compounds of the invention which were prepared.

Table 6 shows results of an aggregation assay using the final compounds.

Table 7 shows those results for known compounds for comparative purpose.

Figure 1B:
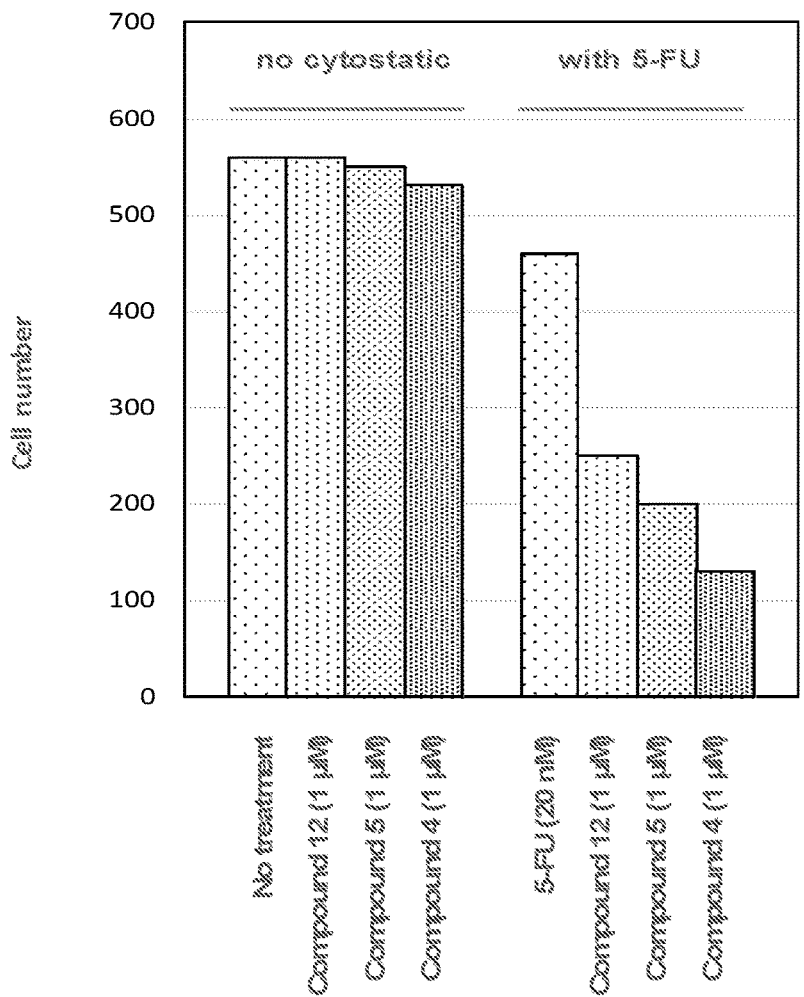

FIGS. 1a and 1b show the results of a chemoresistance assay with two different cell lines for a known cytotoxic and compounds according to the invention (test compounds).

The invention can be executed also as a combination of any of the above named embodiments.

EXAMPLES

General Synthesis Routes:

Reaction scheme A illustrates the general method employed in the synthesis of the compounds of structural formula A-5.

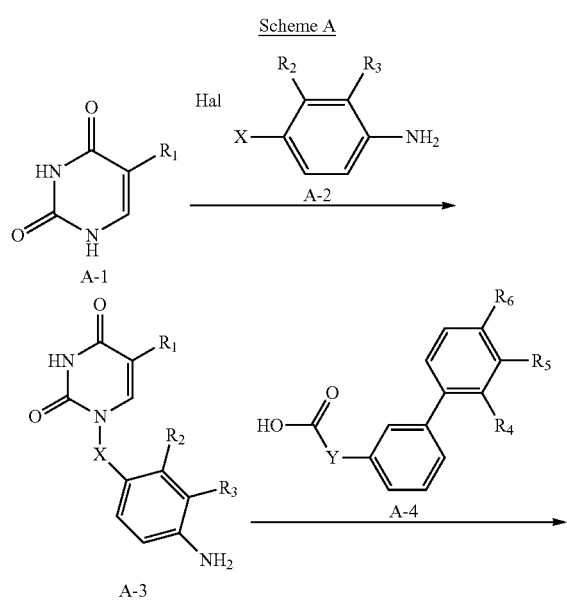

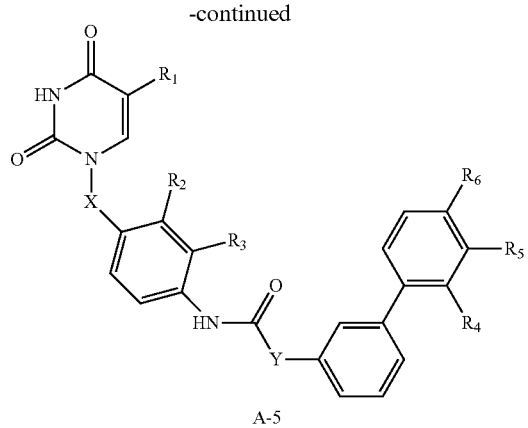

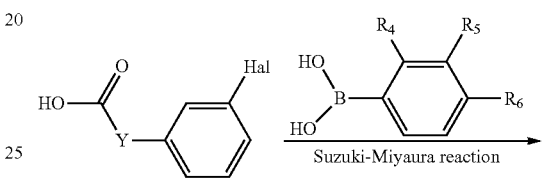

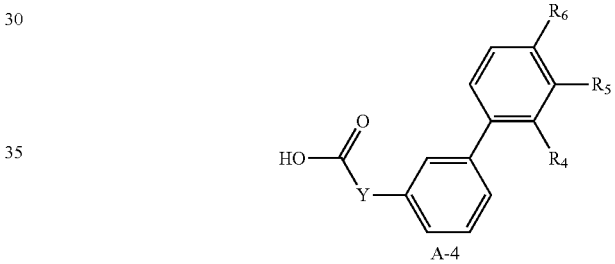

As shown in scheme A, the compounds of structural formula, denoted by A-5 are derived by substitution of a halogenic aromatic ring with an uracil derivative. The building blocks A-4 are got by Suzuki-Miyaura reaction. The final products A-5 were received by amide coupling between amide A-3 and carboxylic acid A-4.

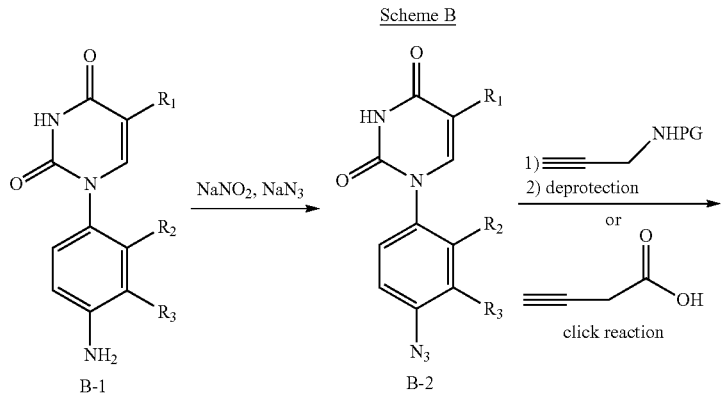

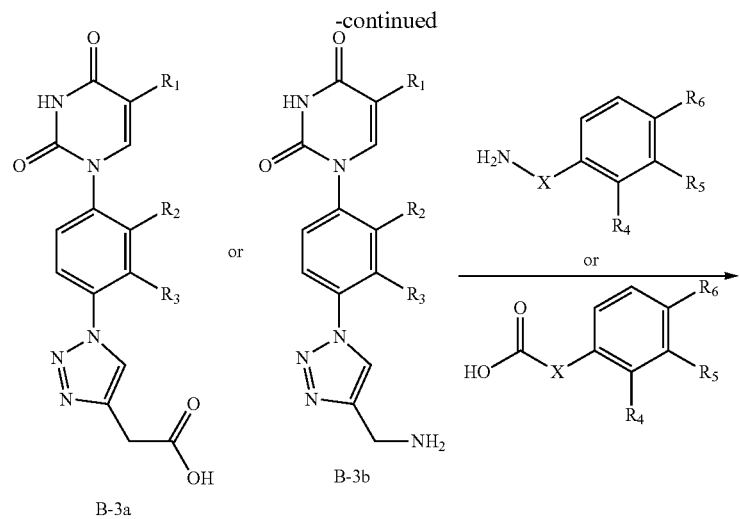

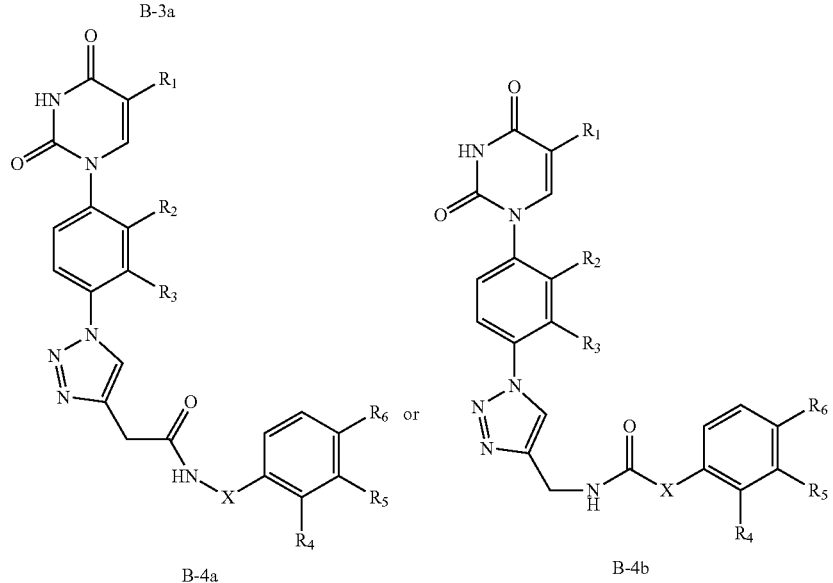

As shown in scheme B the compounds of structural formula denoted by B-4a or B-4b are derived by click chemistry from azide B-2. The final products B-4a or B-4b were received by amide coupling between amide/carboxylic acid and carboxylic acid B-3a or amine B-3b.

The reaction of the compounds of the formula A-3 and B-3a/B-3b to form an amide of the formula A-5/B-4a/b is generally performed in the presence of activating agents, such as PyBOP, EDC, CDI, DCC, EDC, HOAt, HOBt, HATU, TOTU, TBTU or combinations thereof, and optionally an additional base, such as TEA, DIPEA or N-methylmorpholin in an appropriate inert solvent, for example a hydrocarbon or a chlorinate hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, or an ester such as ethyl acetate or ethyl butanoate or an amide such as N,N-dimethylformamide or N,N-dimethylacetamide or N-methyl-pyridone or in a mixture of solvents. The reaction temperature in this case is generally from −20° C. to 100° C., preferably from 0° C. to 25° C. The reaction time is generally from 15 min to 6 days, preferably from 15 min to 16 h, depending on the composition of the mixture and the chosen temperature range. The acids of formula A-4/B-3a can be subjected to the reaction in form of their salts, for example their sodium salts. They can also be transformed into an activated derivative prior to the coupling with the amine, for example into an acid chloride or an acid anhydride by standard transformations. The amines of formula A-3/B-3b can be subjected to the reaction in form of their salts, for example as hydrochloride or triflate salts, in which case usually an additional equivalent of the base is added to the reaction. As far as applicable and unless otherwise indicated, it applies to all acidic or basic compounds occurring in the preparation of the compounds of the formula I that they can be present in form of their salts.

The terms "room temperature" are designate a temperature of about 20° C.

Analytical HPLC Parameters Employed for Characterization of Products.

TABLE 1

HPLC-parameters for characterization of products.

| | |
|---|---|
| method | Waters UPLC BEH C18 |
| column | 2.1 × 50 mm, 1.7 u; 40° C. |
| mobile | A: water + 0.1% FA (formic acid) |
| phase | B: CH$_3$CN + 0.1% FA (formic acid) |

TABLE 1-continued

HPLC-parameters for characterization of products.

| Time (min) | A % | B % |
|---|---|---|
| 0.00 | 100 | 0 |
| 1.0 | 100 | 0 |
| 4.0 | 0 | 100 |
| 5.5 | 100 | 0 |
| 6.0 | 100 | 0 |
| flow rate | 0.5 ml/min | |

Execution Examples: Building Blocks

Building Block BB-1: 1-(4-Aminophenyl)-5-methylpyrimidine-2,4(1H,3H)-dione

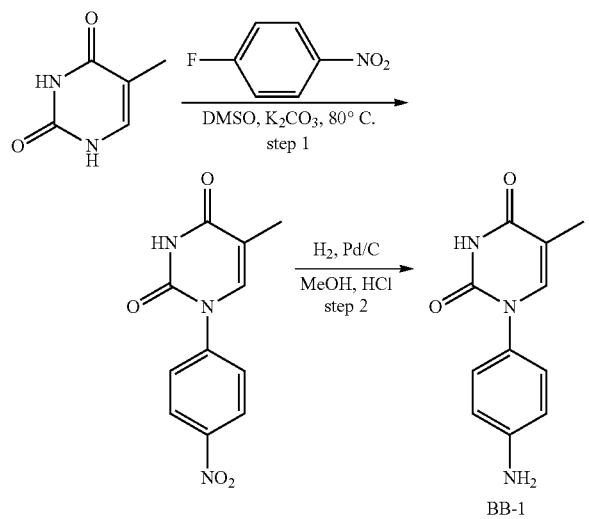

Step 1: 5-Methyl-1-(4-nitrophenyl)pyrimidine-2,4(1H,3H)-dione

A mixture of thymidine (500 mg) and potassium carbonate (260 mg) in DMSO (5.5 ml) is stirred at room temperature for 10 min. Afterwards 4-fluoronitrobenzene (535 mg) in DMSO (5.5 ml) is added and stirred at 80° C. overnight. After cooling to room temperature ethyl acetate and water are added. The water phase is extracted two times with ethyl acetate. The organic phases are dried ($Na_2SO_4$) and concentrated in vacuum to give the desired product. Mass calc. 247.21 g/mol, (ESI) m/z: 246. The compound is used without further purification in the next step.

Step 2: 1-(4-Aminophenyl)-5-methylpyrimidine-2,4(1H,3H)-dione (BB-1)

A suspension of 5-methyl-1-(4-nitrophenyl)pyrimidine-2,4(1H,3H)-dione (699.5 mg) in methanol (200 ml) and conc. HCl (5.8 ml) was degassed three times and ventilated with argon. Afterwards Pd/C is added, again degassed and ventilated with argon and degassed again three times and ventilated with hydrogen. The reaction mixture is stirred overnight under hydrogen at room temperature. Afterwards filtered off over celite and the solvent was removed in vacuum to receive the desired product. (C11H11N3O2)

Mass calc. 217.23 g/mol, (ESI) (M+H)$^+$ m/z: 218. The compound is used without further purification in the next step.

Further Building Blocks According to Synthesis of BB-1

The following building blocks were prepared following a similar procedure as described for building block BB-1 starting from the described building blocks or commercial available building blocks.

TABLE 2

Further Building Blocks prepared (according to synthesis of BB-1)

| No. | Structure | Name | Molecular formula | MS(ESI) m/z (M + H)$^+$ (calc. MS) |
|---|---|---|---|---|
| BB-2 | (structure shown) | 1-(4-Aminophenyl)pyrimidine-2,4(1H,3H)-dione | $C_{10}H_9N_3O_2$ | 204 (203.2 g/mol) |

TABLE 2-continued

Further Building Blocks prepared (according to synthesis of BB-1)

| No. | Structure | Name | Molecular formula | MS(ESI) m/z (M + H)+ (calc. MS) |
|---|---|---|---|---|
| BB-3 | 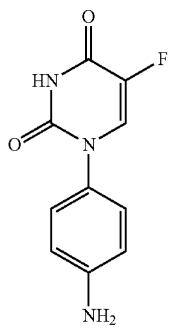 [SMILES: Nc1ccc(-n2cc(F)c(=O)[nH]c2=O)cc1] | 1-(4-Aminophenyl)-5-fluoropyrimidine-2,4(1H,3H)-dione | $C_{10}H_8FN_3O_2$ | 222 (221.19 g/mol) |
| BB-4 | 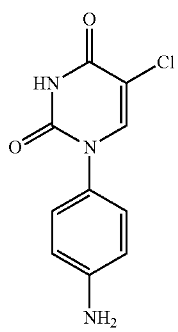 [SMILES: Nc1ccc(-n2cc(Cl)c(=O)[nH]c2=O)cc1] | 1-(4-Aminophenyl)-5-chloropyrimidine-2,4(1H,3H)-dione | $C_{10}H_8ClN_3O_2$ | 238/240 (237.64 g/mol) |
| BB-5 | 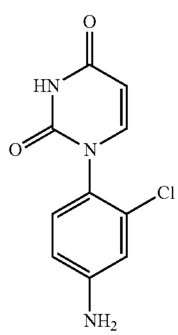 [SMILES: Nc1ccc(-n2ccc(=O)[nH]c2=O)c(Cl)c1] | 1-(4-Amino-2-chlorophenyl)pyrimidine-2,4(1H,3H)-dione | $C_{10}H_8ClN_3O_2$ | 238/240 (237.64 g/mol) |
| BB-6 | 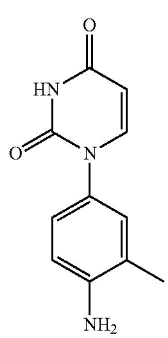 [SMILES: Cc1cc(-n2ccc(=O)[nH]c2=O)ccc1N] | 1-(4-Amino-3-methylphenyl)pyrimidine-2,4(1H,3H)-dione | $C_{11}H_{11}N_3O_2$ | 218 (217.23 g/mol) |

Building Block BB-7: 1-(4-Amino-3-fluorophenyl)pyrimidine-2,4(1H,3H)-dione

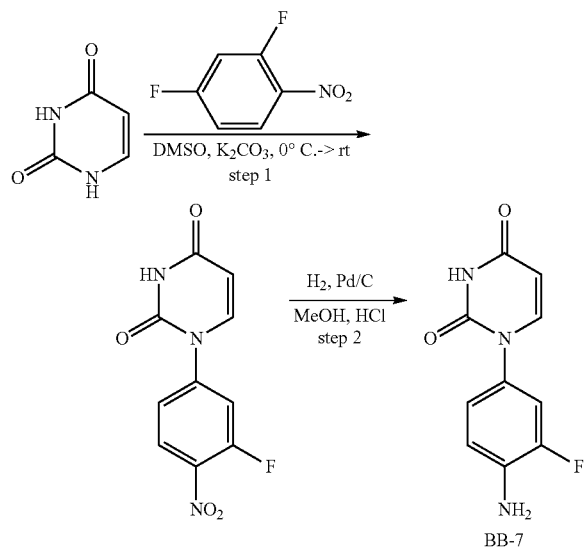

Step 1: 1-(4-Nitro-3-fluorophenyl)pyrimidine-2,4(1H,3H)-dione

A mixture of uracil (100 mg) and potassium carbonate (61.7 mg) in DMSO (1.3 ml) is stirred at room temperature for 10 min. Afterwards it is cooled to 0° C. and 2,4-difluoronitrobenzene (142.2 mg) in DMSO (1.3 ml) is added dropwise. The reaction mixture is allowed to warm up to rt and stirred overnight at this temperature. Ethyl acetate and water are added. The water phase is extracted two times with ethyl acetate. The organic phases were dried ($Na_2SO_4$) and concentrated in vacuum to give the desired product. The organic phase is washed with water, dried ($Na_2SO_4$) and concentrated in vacuum. The residue is purified by preparative normal phase chromatography (n-heptan:ethylacetate 1:1->1:2). The fractions containing the product are evaporated to yield the product as a white solid. Mass calc. 251.17 g/mol, (ESI) m/z: 252

Step 2: 1-(4-Amino-3-fluorophenyl)pyrimidine-2,4(1H,3H)-dione (BB-7)

Step 2 following a similar procedure as described for BB-1 (step 2).
(C10H8FN3O2) Mass calc. 221.19 g/mol, (ESI) (M+H)+ m/z: 222. The compound is used without further purification in the next step.

Building Block BB-8: 1-(3-Aminophenyl)pyrimidine-2,4(1H,3H)-dione

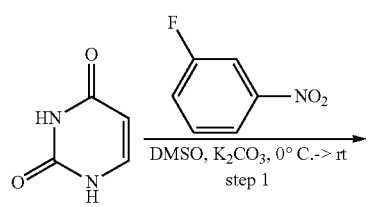

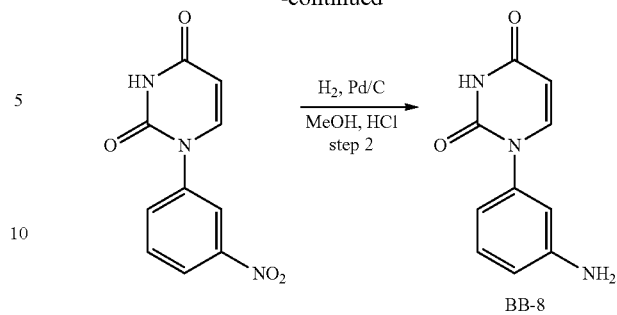

Step 1: 1-(3-Nitrophenyl)pyrimidine-2,4(1H,3H)-dione

A mixture of uracil (100 mg) and potassium carbonate (61.7 mg) in DMSO (1.3 ml) is stirred at room temperature for 10 min. Afterwards 2,4-difluoronitrobenzene (142.2 mg) in DMSO (1.3 ml) is added and stirred at 140° C. overnight. After cooling to room temperature ethyl acetate and water are added. The water phase is extracted two times with ethyl acetate. The organic phases are dried ($Na_2SO_4$) and concentrated in vacuum to give the desired product. ($C_{10}H7N_3O_4$) Mass calc. 233.18 g/mol, (ESI) m/z: 234. The compound is used without further purification in the next step.

Step 2: 1-(4-Aminophenyl)pyrimidine-2,4(1H,3H)-dione (BB-8)

Step 2 following a similar procedure as described for BB-1 (step 2).
(C10H9N3O2) Mass calc. 203.2 g/mol, (ESI) (M+H)+ m/z: 204. The compound is used without further purification in the next step.

Building Block BB-9: 1-(4-Aminobenzyl)pyrimidine-2,4(1H,3H)-dione

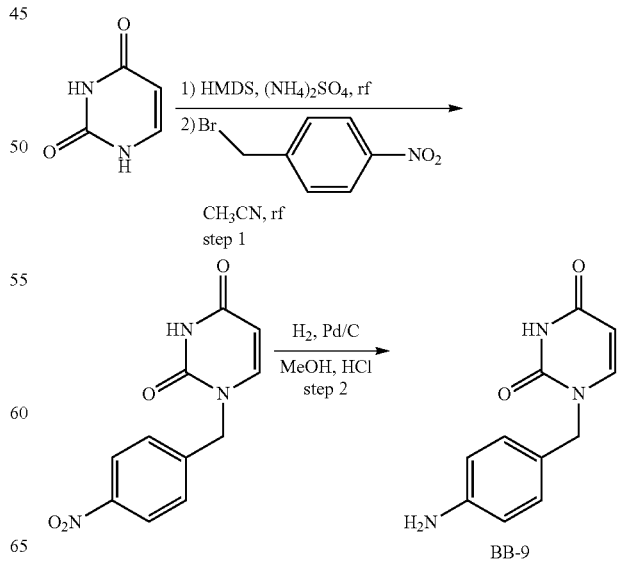

Step 1:
1-(4-Nitrobenzyl)pyrimidine-2,4(1H,3H)-dione

Compound is synthesized as described from E. Snip et al. *Tetrahedron* 2002, 58, 8863-8873

Step 2:
1-(4-Aminobenzyl)pyrimidine-2,4(1H,3H)-dione

Step 2 following a similar procedure as described for BB-1 (step 2).

(C11H11N$_3$O2) Mass calc. 217.23 g/mol, (ESI) (M+H)$^+$ m/z: 218. The compound is used without further purification in the next step.

Building Block BB-10: 2-(4'-Chloro-[1,1'-biphenyl]-3-yl)acetic acid

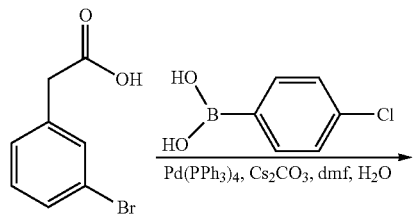

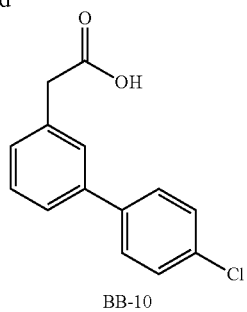

BB-10

To a degassed solution of 2-(3-bromophenyl)acetic acid (50 mg) in DMF (755 µl) Pd(PPh$_3$)$_4$ (2.7 mg) is added. The reaction mixture is stirred for 10 min at room temperature. Afterwards phenyl boronic acid (39.9 mg), Cs$_2$CO$_3$ (148.5 mg) and water (223 µl) are added. The reaction mixture is stirred at 80° C. for 4 hours. After cooling to room temperature ethyl acetate and water are added. The water phase is acidified with 2 M HCl solution. The water layer is extracted with ethyl acetate. The organic layers are dried (Na$_2$SO$_4$) then concentrated in vacuum to give the desired product.

Mass calc. 246.69 g/mol, (ESI) m/z (M–H)$^-$: 244. (C14H11ClO2) The compound is used without further purification in the next step.

Further Building Blocks According to Synthesis of BB-10

The following building blocks were prepared following a similar procedure as described for BB-10 starting from the described building blocks or commercial available building blocks.

TABLE 3

Further building blocks prepared (according to synthesis of BB-10)

| No. | Structure | Name | Molecular formula | MS(ESI), m/z (M – H)$^-$ |
|---|---|---|---|---|
| BB-11 | 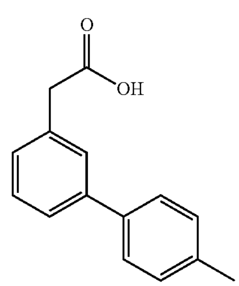 [SMILES: Cc1ccc(-c2cccc(CC(=O)O)c2)cc1] | 2-(4'-methyl-[1,1'-biphenyl]-3-yl)acetic acid | C$_{15}$H$_{14}$O$_2$ | 224 (226.28 g/mol) |
| BB-12 | 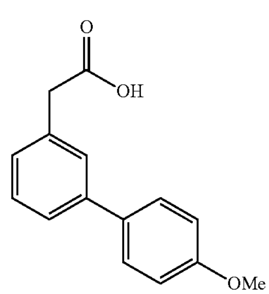 [SMILES: COc1ccc(-c2cccc(CC(=O)O)c2)cc1] | 2-(4'-methoxy-[1,1'-biphenyl]-3-yl)acetic acid | C$_{15}$H$_{14}$O$_3$ | 241 (242.27 g/mol) |

TABLE 3-continued

Further building blocks prepared (according to synthesis of BB-10)

| No. | Structure | Name | Molecular formula | MS(ESI), m/z (M − H)⁻ |
|---|---|---|---|---|
| BB-13 | 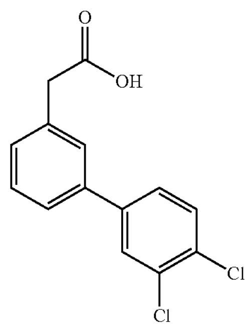 [SMILES: O=C(O)Cc1cccc(-c2ccc(Cl)c(Cl)c2)c1] | 2-(3',4'-dichloro-[1,1'-biphenyl]-3-yl)acetic acid | $C_{14}H_{10}Cl_2O_2$ | 279/281 (281.13 g/mol) |
| BB-14 | 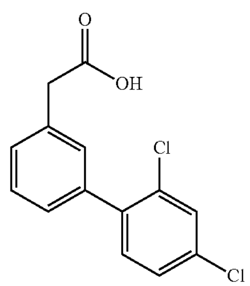 [SMILES: O=C(O)Cc1cccc(-c2ccc(Cl)cc2Cl)c1] | 2-(2',4'-dichloro-[1,1'-biphenyl]-3-yl)acetic acid | $C_{14}H_{10}Cl_2O_2$ | 278/280 (281.13 g/mol) |
| BB-15 | 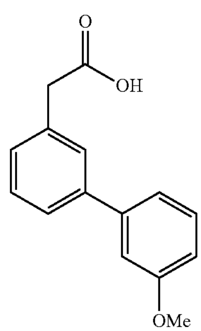 [SMILES: COc1cccc(-c2cccc(CC(=O)O)c2)c1] | 2-(3'-methoxy-[1,1'-biphenyl]-3-yl)acetic acid | $C_{15}H_{14}O_3$ | 240 (242.27 g/mol) |
| BB-16 | 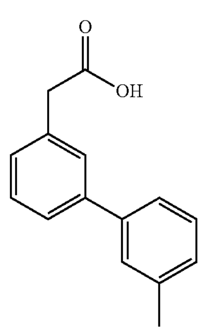 [SMILES: Cc1cccc(-c2cccc(CC(=O)O)c2)c1] | 2-(3'-methyl-[1,1'-biphenyl]-3-yl)acetic acid | $C_{15}H_{14}O_2$ | 225 (226.28 g/mol) |

TABLE 3-continued

Further building blocks prepared (according to synthesis of BB-10)

| No. | Structure | Name | Molecular formula | MS(ESI), m/z (M − H)⁻ |
|---|---|---|---|---|
| BB-17 | 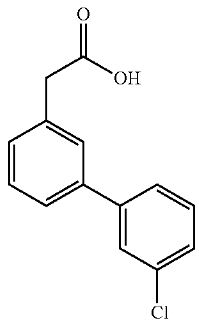 [SMILES: O=C(O)Cc1cccc(-c2cccc(Cl)c2)c1] | 2-(3'-chloro-[1,1'-biphenyl]-3-yl)acetic acid | $C_{14}H_{11}ClO_2$ | 244 (246.69 g/mol) |
| BB-18 | 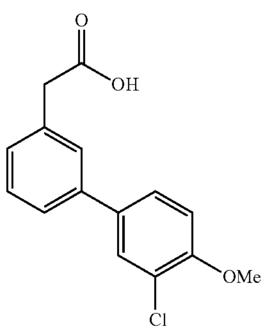 [SMILES: COc1ccc(-c2cccc(CC(=O)O)c2)cc1Cl] | 2-(3'-chloro-4'-methoxy-[1,1'-biphenyl]-3-yl)acetic acid | $C_{15}H_{13}ClO_3$ | 274 (276.72 g/mol) |
| BB-19 | 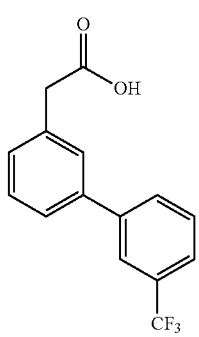 [SMILES: O=C(O)Cc1cccc(-c2cccc(C(F)(F)F)c2)c1] | 2-(3'-(trifluoromethyl)-[1,1'-biphenyl]-3-yl)acetic acid | $C_{15}H_{11}F_3O_2$ | 279 (280.25 g/mol) |

TABLE 3-continued

Further building blocks prepared (according to synthesis of BB-10)

| No. | Structure | Name | Molecular formula | MS(ESI), m/z (M − H)⁻ |
|---|---|---|---|---|
| BB-20 | 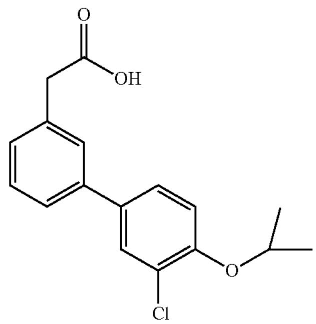 [SMILES: CC(C)Oc1ccc(-c2cccc(CC(=O)O)c2)cc1Cl] | 2-(3'-chloro-4'-isopropoxy-[1,1'-biphenyl]-3-yl)acetic acid | $C_{17}H_{17}ClO_3$ | 303 (304.77 g/mol) |
| BB-21 | 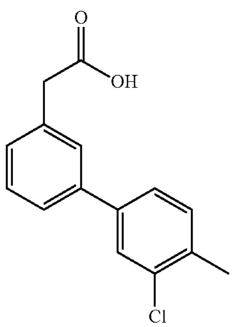 [SMILES: Cc1ccc(-c2cccc(CC(=O)O)c2)cc1Cl] | 2-(3'-chloro-4'-methyl-[1,1'-biphenyl]-3-yl)acetic acid | $C_{15}H_{13}ClO_2$ | 259 (260.72 g/mol) |
| BB-22 | 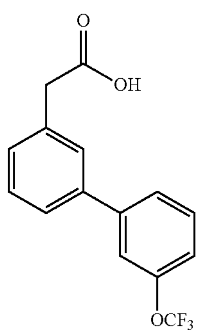 [SMILES: O=C(O)Cc1cccc(-c2cccc(OC(F)(F)F)c2)c1] | 2-(3'-(trifluoromethoxy)-[1,1'-biphenyl]-3-yl)acetic acid | $C_{15}H_{11}F_3O_3$ | 294 (296.25 g/mol) |

Building Block BB-23: 3'-Methoxy-[1,1'-biphenyl]-3-carboxylic acid

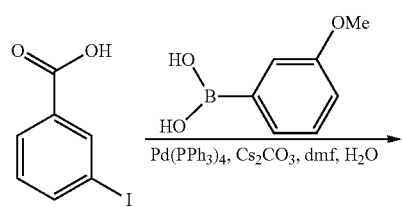

-continued

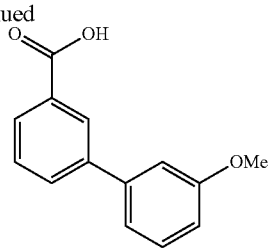

BB-23

To a degassed solution of 3-iodobenzoic acid (173.6 mg) in DMF (2.3 ml) Pd(PPh$_3$)$_4$ (8.2 mg) is added. The reaction mixture is stirred for 10 min at room temperature. Afterwards phenyl boronic acid (117 mg), Cs$_2$CO$_3$ (445.5 mg) and water (0.83 ml) are added. The reaction mixture is stirred at 80° C. for 4 hours. After cooling to room temperature ethyl acetate and water are added. The water phase is acidified with 2 M HCl solution. The water layer is extracted with ethyl acetate. The organic layers are dried (Na₂SO₄) then concentrated in vacuum to give the desired product.

Mass calc. 228.25 g/mol, (ESI) (M–H)⁻ m/z: 226. (C14H12O3) The compound is used without further purification in the next step.

TABLE 4

Further Building Blocks prepared (according to synthesis of BB-23)

| No. | Structure | Name | Molecular formula | MS(ESI) m/z (M − H)⁻ |
|---|---|---|---|---|
| BB-24 | 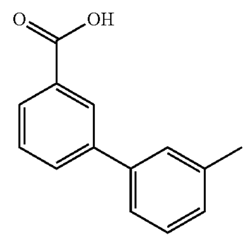 [SMILES: Cc1cccc(-c2cccc(C(=O)O)c2)c1] | 3'-methyl-[1,1'-biphenyl]-3-carboxylic acid | $C_{14}H_{12}O_2$ | 211 (212.25 g/mol) |
| BB-25 | 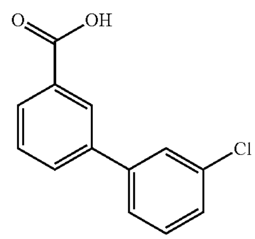 [SMILES: O=C(O)c1cccc(-c2cccc(Cl)c2)c1] | 3'-chloro-[1,1'-biphenyl]-3-carboxylic acid | $C_{13}H_9ClO_2$ | 230/232 (232.66 g/mol) |
| BB-26 | 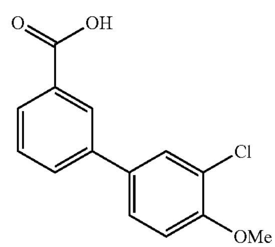 [SMILES: COc1ccc(-c2cccc(C(=O)O)c2)cc1Cl] | 3'-chloro-4'-methoxy-[1,1'-biphenyl]-3-carboxylic acid | $C_{14}H_{11}ClO_3$ | 261 (262.69 g/mol) |
| BB-27 | 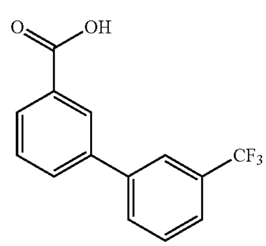 [SMILES: O=C(O)c1cccc(-c2cccc(C(F)(F)F)c2)c1] | 3'-(trifluoromethyl)-[1,1'-biphenyl]-3-carboxylic acid | $C_{14}H_9F_3O_2$ | 264 (266.22 g/mol) |
| BB-28 | 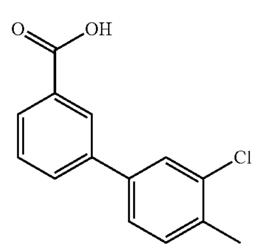 [SMILES: Cc1ccc(-c2cccc(C(=O)O)c2)cc1Cl] | 3'-chloro-4'-methyl-[1,1'-biphenyl]-3-carboxylic acid | $C_{14}H_{11}ClO_2$ | 245/247 (246.69 g/mol) |

TABLE 4-continued

Further Building Blocks prepared (according to synthesis of BB-23)

| No. | Structure | Name | Molecular formula | MS(ESI) m/z (M − H)⁻ |
|---|---|---|---|---|
| BB-29 | 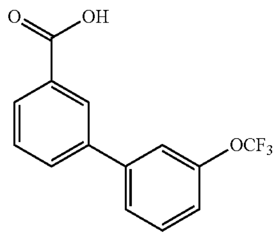 [SMILES: O=C(O)c1cccc(-c2cccc(OC(F)(F)F)c2)c1] | 3'-(trifluoromethoxy)-[1,1'-biphenyl]-3-carboxylic acid | $C_{14}H_9F_3O_3$ | 280 (282.22 g/mol) |
| BB-30 | 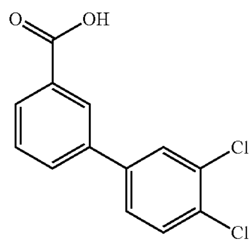 [SMILES: O=C(O)c1cccc(-c2ccc(Cl)c(Cl)c2)c1] | 3',4'-dichloro-[1,1'-biphenyl]-3-carboxylic acid | $C_{13}H_8Cl_2O_2$ | 265/267/269 (267.11 g/mol) |

Execution Examples: Final Compounds

Compound 1: 2-(3'-Chloro-4'-methoxy-[1,1'-biphenyl]-3-yl)-N-(4-(5-methyl-2,4-dioxo-3,4-dihydropyrimidin-1(2H)-yl)phenyl)acetamide

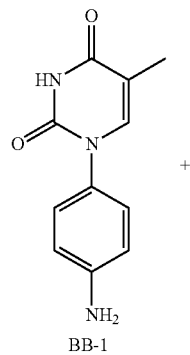

BB-1

+

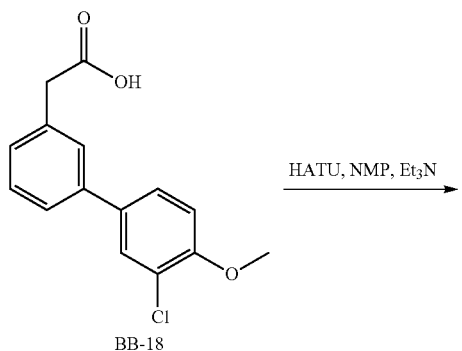

BB-18

HATU, NMP, Et₃N →

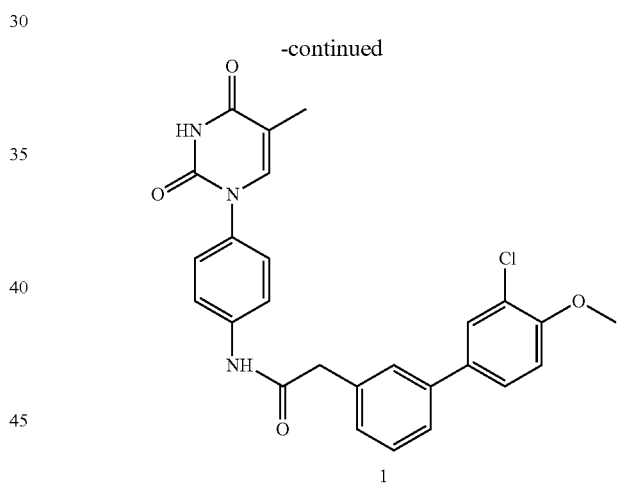

1

To a solution of BB-18 (30.7 mg), HATU (32.2 mg) in NMP (250 μl) are added BB-1 (16.1 mg) and triethylamine (11 μl). The reaction mixture is stirred over night at room temperature. Ethyl acetate is added and washed with water. The organic layers are dried (Na₂SO₄) and concentrated in vacuum. The residue is purified by normal phase chromatography (CH₂Cl₂:MeOH:Et₃N (20:1:0.1)). The fractions containing the product are evaporated to yield a white solid. ($C_{28}H_2N_2O$), LCMS Rt=3.1 min; Mass calc. 475.93 g/mol; MS (ESI) m/z: 476 (M+H)⁺.

The following compounds were prepared in a similar procedure as described for compound 1 starting from the described building blocks or commercial available building blocks.

TABLE 5

Further compounds prepared (according to synthesis of compound 1)

| No | Structure | Name | Molecular formula | MS(ESI) m/z (M + H)+ (Calc Mass) |
|---|---|---|---|---|
| 2 BB-1 + BB-17 | | 2-(3'-chloro-[1,1'-biphenyl]-3-yl)-N-(4-(5-methyl-2,4-dioxo-3,4-dihydro-pyrimidin-1(2H)-yl)phenyl)acetamide | C25H20ClN3O3 | 445/447 $R_t$ = 3.18 (445.9 g/mol) |
| 3 BB-1 + BB-13 | | 2-(3',4'-dichloro-[1,1'-biphenyl]-3-yl)-N-(4-(5-methyl-2,4-dioxo-3,4-dihydro-pyrimidin-1(2H)-yl)phenyl)acetamide | C25H19Cl2N3O3 | 480/482 $R_t$ = 3.33 (480.35 g/mol) |
| 4 BB-2 + BB-13 | | 2-(3',4'-dichloro-[1,1'-biphenyl]-3-yl)-N-(4-(2,4-dioxo-3,4-dihydro-pyrimidin-1(2H)-yl)phenyl)acetamide | C24H17Cl2N3O3 | 466/468 $R_t$ = 3.68 (466.32 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 5 | BB-2 + BB-14 | 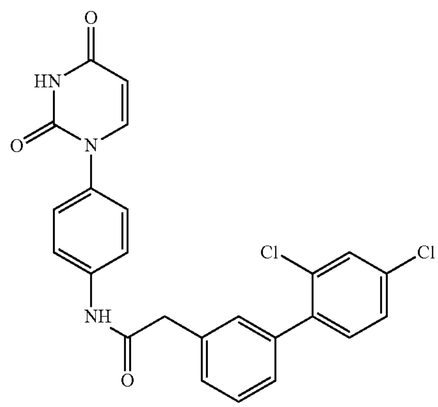 [SMILES: O=C(Cc1cccc(-c2ccc(Cl)cc2Cl)c1)Nc1ccc(-n2ccc(=O)[nH]c2=O)cc1] | 2-(2',4'-dichloro-[1,1'-biphenyl]-3-yl)-N-(4-(2,4-dioxo-3,4-dihydro-pyrimidin-1(2H)-yl)phenyl)acetamide | C24H17Cl2N3O3 | 465/467 $R_t$ = 3.22 (466.32 g/mol) |
| 6 | BB-1 + BB-21 | 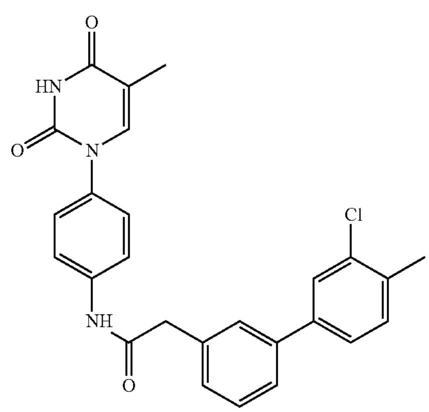 [SMILES: Cc1ccc(-c2cccc(CC(=O)Nc3ccc(-n4cc(C)c(=O)[nH]c4=O)cc3)c2)cc1Cl] | 2-(3'-chloro-4'-methyl-[1,1'-biphenyl]-3-yl)-N-(4-(5-methyl-2,4-dioxo-3,4-dihydropyrimidin-1(2H)-yl)phenyl)acetamide | C26H22ClN3O3 | 460 $R_t$ = 3.53 (459.93 g/mol) |
| 7 | BB-1 + BB-14 | 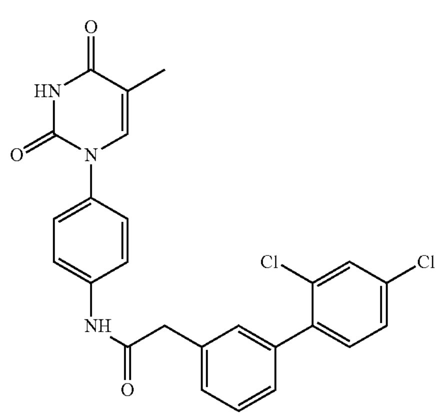 [SMILES: Cc1cn(-c2ccc(NC(=O)Cc3cccc(-c4ccc(Cl)cc4Cl)c3)cc2)c(=O)[nH]c1=O] | 2-(2',4'-dichloro-[1,1'-biphenyl]-3-yl)-N-(4-(5-methyl-2,4-dioxo-3,4-dihydro-pyrimidin-1(2H)-yl)phenyl)acetamide | C25H19Cl2N3O3 | 480/482 $R_t$ = 3.3 (480.35 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 8 | BB-2 + BB-20 | 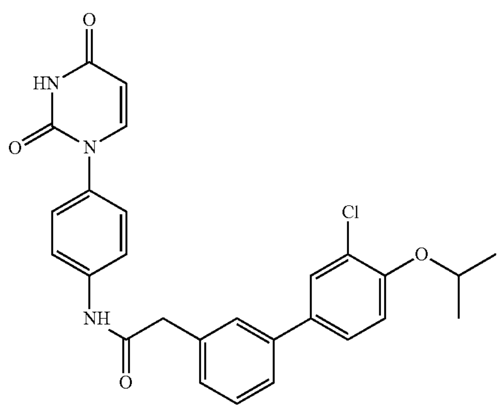 [SMILES: CC(C)Oc1ccc(-c2cccc(CC(=O)Nc3ccc(-n4ccc(=O)[nH]c4=O)cc3)c2)cc1Cl] | 2-(3'-chloro-4'-isopropoxy-[1,1'-biphenyl]-3-yl)-N-(4-(2,4-dioxo-3,4-dihydro-pyrimidin-1(2H)-yl)phenyl)acetamide | C27H24ClN3O4 | 490 R$_t$ = 3.35 (489.96 g/mol) |
| 9 | BB-1 + BB-19 | 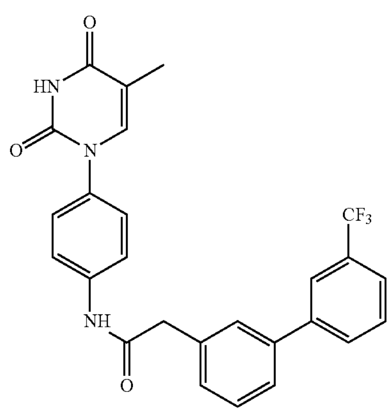 [SMILES: Cc1cn(-c2ccc(NC(=O)Cc3cccc(-c4cccc(C(F)(F)F)c4)c3)cc2)c(=O)[nH]c1=O] | N-(4-(5-methyl-2,4-dioxo-3,4-dihydro-pyrimidin-1(2H)-yl)phenyl)-2-(3'-(trifluoromethyl)-[1,1'-biphenyl]-3-yl)acetamide | C26H20F3N3O3 | 479 R$_t$ = 3.23 (479.46 g/mol) |
| 10 | BB-6 + BB-21 | 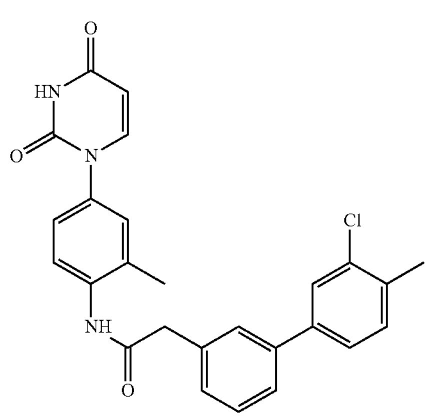 [SMILES: Cc1ccc(-c2cccc(CC(=O)Nc3ccc(-n4ccc(=O)[nH]c4=O)cc3C)c2)cc1Cl] | 2-(3'-chloro-4'-methyl-[1,1'-biphenyl]-3-yl)-N-(4-(2,4-dioxo-3,4-dihydro-pyrimidin-1(2H)-yl)-2-methyl-phenyl)acetamide | C26H22ClN3O3 | 460/462 R$_t$ = 3.28 (459.93 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 11 | BB-1 + BB-22 | 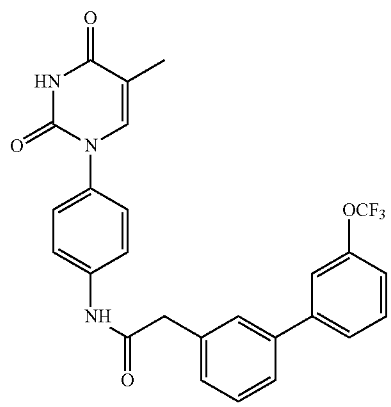 [SMILES: Cc1cn(-c2ccc(NC(=O)Cc3cccc(-c4cccc(OC(F)(F)F)c4)c3)cc2)c(=O)[nH]c1=O] | N-(4-(5-methyl-2,4-dioxo-3,4-dihydro-pyrimidin-1(2H)-yl)phenyl)-2-(3'-(trifluoro-methoxy)-[1,1'-biphenyl]-3-yl)acetamide | C26H20F3N3O4 | 496 $R_t$ = 3.28 (459.46 g/mol) |
| 12 | BB-3 + BB-13 | 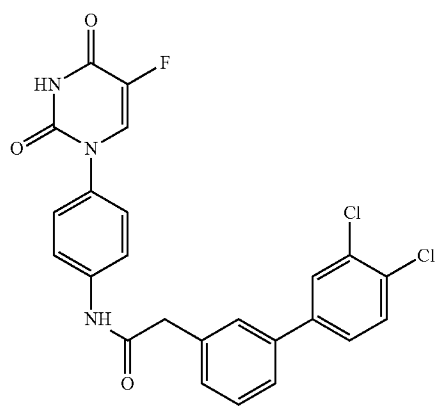 [SMILES: O=C(Cc1cccc(-c2ccc(Cl)c(Cl)c2)c1)Nc1ccc(-n2cc(F)c(=O)[nH]c2=O)cc1] | 2-(3',4'-dichloro-[1,1'-biphenyl]-3-yl)-N-(4-(5-fluoro-2,4-dioxo-3,4-dihydro-pyrimidin-1(2H)-yl)phenyl)acetamide | C24H16Cl2FN3O3 | 484/486 $R_t$ = 3.3 (484.31 g/mol) |
| 13 | BB-5 + BB-18 | 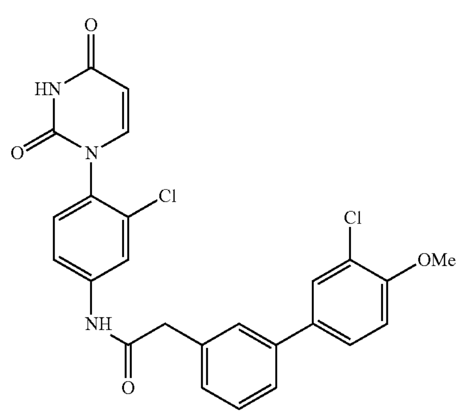 [SMILES: COc1ccc(-c2cccc(CC(=O)Nc3ccc(-n4ccc(=O)[nH]c4=O)c(Cl)c3)c2)cc1Cl] | 2-(3'-chloro-4'-methoxy-[1,1'-biphenyl]-3-yl)-N-(3-chloro-4-(2,4-dioxo-3,4-dihydro-pyrimidin-1(2H)-yl)phenyl)acetamide | C25H19Cl2N3O4 | 496/498 $R_t$ = 3.18 (496.34 g/mol) |

TABLE 5-continued

Further compounds prepared (according to synthesis of compound 1)

| No | Structure | Name | Molecular formula | MS(ESI) m/z (M + H)+ (Calc Mass) |
|---|---|---|---|---|
| 14 | BB-6 + BB-18 | 2-(3'-chloro-4'-methoxy-[1,1'-biphenyl]-3-yl)-N-(4-(2,4-dioxo-3,4-dihydropyrimidin-1(2H)-yl)-2-methylphenyl)acetamide | C26H22ClN3O4 | 476 R$_t$ = 3.07 (475.93 g/mol) |
| 15 | BB-1 + BB-10 | 2-(4'-chloro-[1,1'-biphenyl]-3-yl)-N-(4-(5-methyl-2,4-dioxo-3,4-dihydropyrimidin-1(2H)-yl)phenyl)acetamide | C25H20ClN3O3 | 446 R$_t$ = 3.18 (445.9 g/mol) |
| 16 | BB-3 + BB-10 | 2-(4'-chloro-[1,1'-biphenyl]-3-yl)-N-(4-(5-fluoro-2,4-dioxo-3,4-dihydropyrimidin-1(2H)-yl)phenyl)acetamide | C24H17ClFN3O3 | 450 R$_t$ = 2.82 (449.87 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 17 | BB-4 + BB-22 | 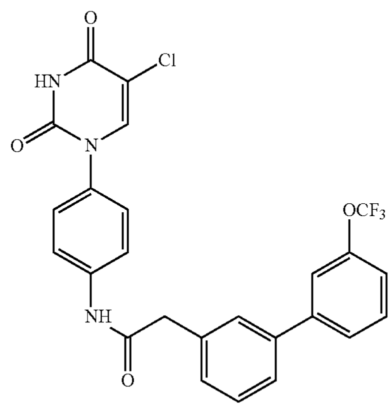 [SMILES: O=C(Cc1cccc(-c2cccc(OC(F)(F)F)c2)c1)Nc1ccc(-n2cc(Cl)c(=O)[nH]c2=O)cc1] | N-(4-(5-chloro-2,4-dioxo-3,4-dihydro-pyrimidin-1(2H)-yl)phenyl)-2-(3'-(trifluoro-methoxy)-[1,1'-biphenyl]-3-yl)acetamide | C25H17ClF3N3O4 | 516 $R_t$ = 3.37 (515.87 g/mol) |
| 18 | BB-6 + BB-13 | 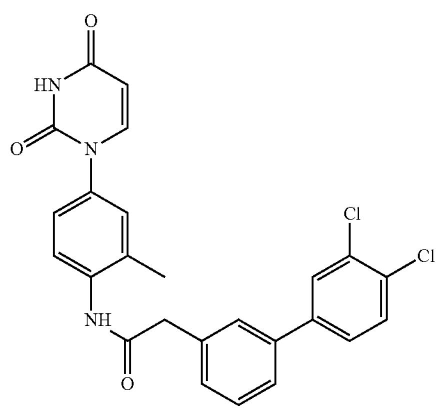 [SMILES: Cc1cc(-n2ccc(=O)[nH]c2=O)ccc1NC(=O)Cc1cccc(-c2ccc(Cl)c(Cl)c2)c1] | 2-(3',4'-dichloro-[1,1'-biphenyl]-3-yl)-N-(4-(2,4-dioxo-3,4-dihydro-pyrimidin-1(2H)-yl)-2-methyl-phenyl)acetamide | C25H19Cl2N3O3 | 480/482 $R_t$ = 3.30 (480.35 g/mol) |
| 19 | BB-2 + BB-22 | 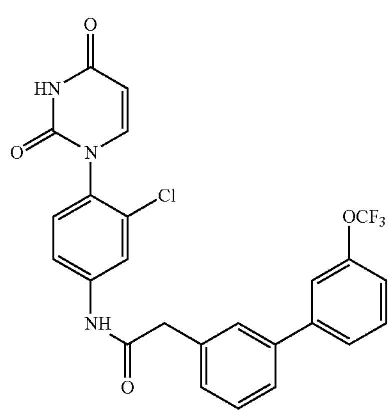 [SMILES: O=C(Cc1cccc(-c2cccc(OC(F)(F)F)c2)c1)Nc1ccc(-n2ccc(=O)[nH]c2=O)c(Cl)c1] | N-(3-chloro-4-(2,4-dioxo-3,4-dihydro-pyrimidin-1(2H)-yl)phenyl)-2-(3'-(trifluoro-methoxy)-[1,1'-biphenyl]-3-yl)acetamide | C25H17ClF3N3O4 | 516 $R_t$ = 3.35 (515.87 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 20 | BB-3 + BB-14 | 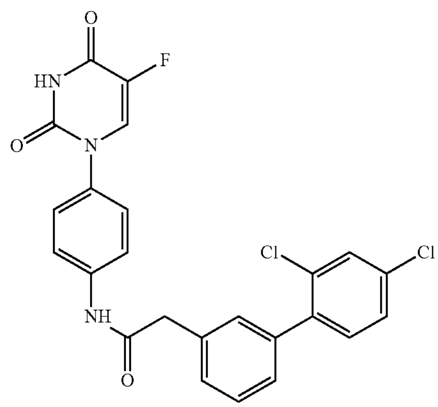 [SMILES: O=C(Cc1cccc(-c2ccc(Cl)cc2Cl)c1)Nc1ccc(-n2cc(F)c(=O)[nH]c2=O)cc1] | 2-(2',4'-dichloro-[1,1'-biphenyl]-3-yl)-N-(4-(5-fluoro-2,4-dioxo-3,4-dihydro-pyrimidin-1(2H)-yl)phenyl)acetamide | C24H16Cl2FN3O3 | 485 $R_t$ = 3.27 (484.31 g/mol) |
| 21 | BB-5 + BB-13 | 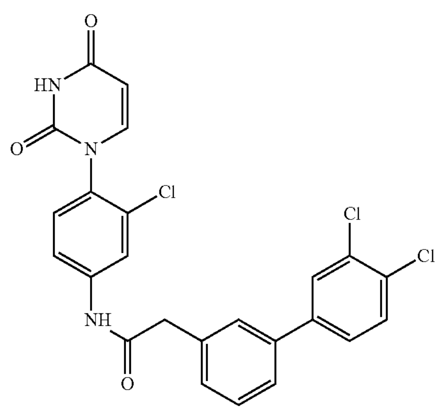 [SMILES: O=C(Cc1cccc(-c2ccc(Cl)c(Cl)c2)c1)Nc1ccc(-n2ccc(=O)[nH]c2=O)c(Cl)c1] | N-(3-chloro-4-(2,4-dioxo-3,4-dihydro-pyrimidin-1(2H)-yl)phenyl)-2-(3',4'-dichloro-[1,1'-biphenyl]-3-yl)acetamide | C24H16Cl3N3O3 | 500/502 $R_t$ = 3.38 (500.76 g/mol) |
| 22 | BB-1 + BB-15 | 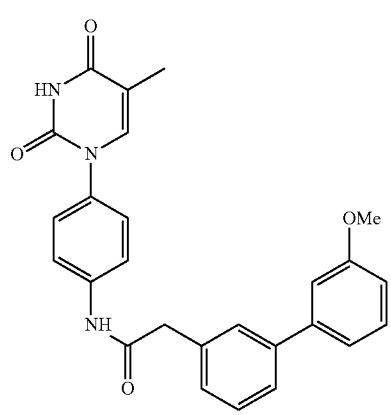 [SMILES: COc1cccc(-c2cccc(CC(=O)Nc3ccc(-n4cc(C)c(=O)[nH]c4=O)cc3)c2)c1] | 2-(3'-methoxy-[1,1'-biphenyl]-3-yl)-N-(4-(5-methyl-2,4-dioxo-3,4-dihydro-pyrimidin-1(2H)-yl)phenyl)acetamide | C26H23N3O4 | 442 $R_t$ = 3.02 (441.49 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 23 | BB-1 + BB-20 | 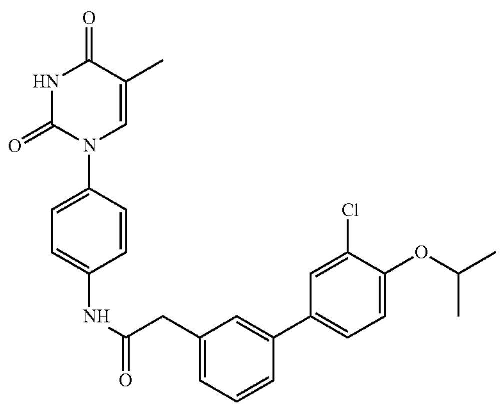 [SMILES: Cc1cn(-c2ccc(NC(=O)Cc3cccc(-c4ccc(OC(C)C)c(Cl)c4)c3)cc2)c(=O)[nH]c1=O] | 2-(3'-chloro-4'-isopropoxy-[1,1'-biphenyl]-3-yl)-N-(4-(5-methyl-2,4-dioxo-3,4-dihydropyrimidin-1(2H)-yl)phenyl)acetamide | C28H26ClN3O4 | 504 $R_t$ = 3.70 (503.93 g/mol) |
| 24 | BB-2 + BB-10 | 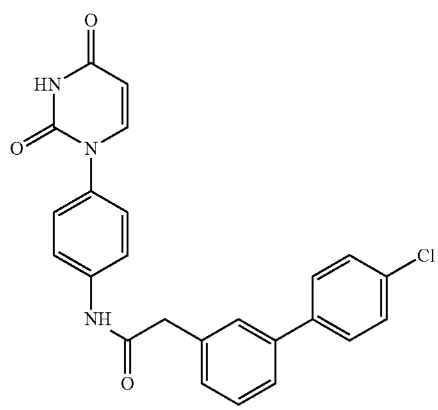 [SMILES: O=C(Cc1cccc(-c2ccc(Cl)cc2)c1)Nc1ccc(-n2ccc(=O)[nH]c2=O)cc1] | 2-(4'-chloro-[1,1'-biphenyl]-3-yl)-N-(4-(2,4-dioxo-3,4-dihydro-pyrimidin-1(2H)-yl)phenyl)acetamide | C24H18ClN3O3 | 433 $R_t$ = 3.10 (431.88 g/mol) |
| 25 | BB-7 + BB-18 | 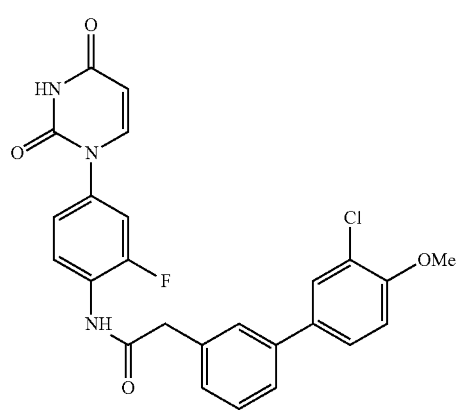 [SMILES: COc1ccc(-c2cccc(CC(=O)Nc3ccc(-n4ccc(=O)[nH]c4=O)cc3F)c2)cc1Cl] | 2-(3'-chloro-4'-methoxy-[1,1'-biphenyl]-3-yl)-N-(4-(2,4-dioxo-3,4-dihydro-pyrimidin-1(2H)-yl)-2-fluoro-phenyl)acetamide | C25H19ClFN3O4 | 482 $R_t$ = 3.07 (479.89 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 26 | BB-2 + BB-17 | 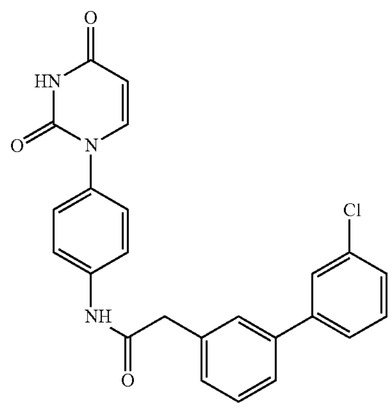 [SMILES: O=C(Cc1cccc(-c2cccc(Cl)c2)c1)Nc1ccc(-n2ccc(=O)[nH]c2=O)cc1] | 2-(3'-chloro-[1,1'-biphenyl]-3-yl)-N-(4-(2,4-dioxo-3,4-dihydro-pyrimidin-1(2H)-yl)phenyl)acetamide | C24H18ClN3O3 | 432 R$_t$ = 3.10 (431.88 g/mol) |
| 27 | BB-2 + BB-18 | 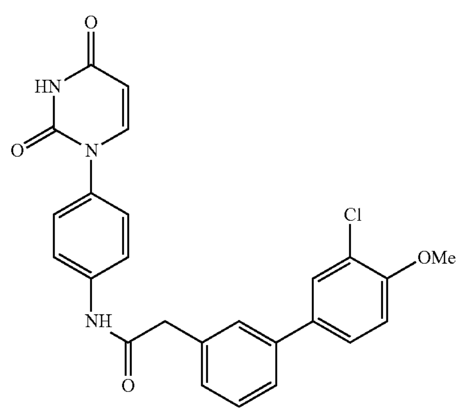 [SMILES: COc1ccc(-c2cccc(CC(=O)Nc3ccc(-n4ccc(=O)[nH]c4=O)cc3)c2)cc1Cl] | 2-(3'-chloro-4'-methoxy-[1,1'-biphenyl]-3-yl)-N-(4-(2,4-dioxo-3,4-dihydro-pyrimidin-1(2H)-yl)phenyl)acetamide | C25H20ClN3O4 | 461/463 R$_t$ = 3.02 (461.9 g/mol) |
| 28 | BB-7 + BB-22 | 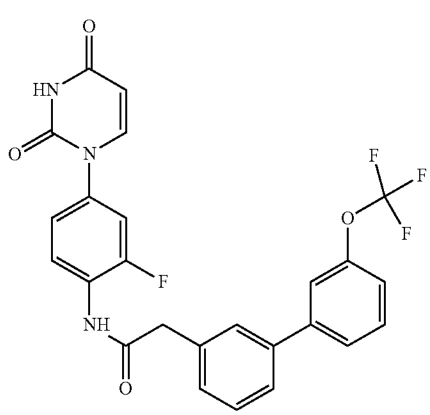 [SMILES: O=C(Cc1cccc(-c2cccc(OC(F)(F)F)c2)c1)Nc1ccc(-n2ccc(=O)[nH]c2=O)cc1F] | N-(4-(2,4-dioxo-3,4-dihydro-pyrimidin-1(2H)-yl)-2-fluoro-phenyl)-2-(3'-(trifluoro-methoxy)-[1,1'-biphenyl]-3-yl)acetamide | C25H17F4N3O4 | 502 R$_t$ = 3.23 (499.42 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 29 | BB-2 + BB-21 | 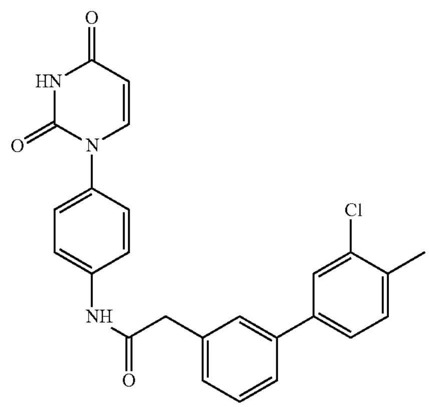 [SMILES: Cc1ccc(-c2cccc(CC(=O)Nc3ccc(-n4ccc(=O)[nH]c4=O)cc3)c2)cc1Cl] | 2-(3'-chloro-4'-methyl-[1,1'-biphenyl]-3-yl)-N-(4-(2,4-dioxo-3,4-dihydro-pyrimidin-1(2H)-yl)phenyl)acetamide | C25H20ClN3O3 | 446 $R_t$ = 3.33 (445.9 g/mol) |
| 30 | BB-4 + BB-18 | 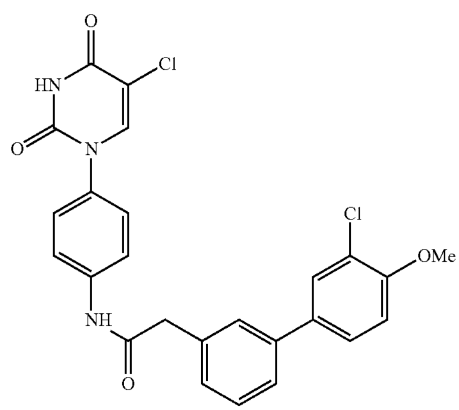 [SMILES: COc1ccc(-c2cccc(CC(=O)Nc3ccc(-n4cc(Cl)c(=O)[nH]c4=O)cc3)c2)cc1Cl] | N-(4-(5-chloro-2,4-dioxo-3,4-dihydro-pyrimidin-1(2H)-yl)phenyl)-2-(3'-chloro-4'-methoxy-[1,1'-biphenyl]-3-yl)acetamide | C25H19Cl2N3O4 | 496/498 $R_t$ = 3.22 (496.34 g/mol) |
| 31 | BB-1 + BB-12 | 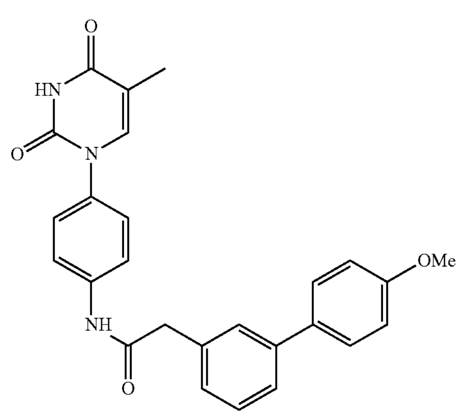 [SMILES: COc1ccc(-c2cccc(CC(=O)Nc3ccc(-n4cc(C)c(=O)[nH]c4=O)cc3)c2)cc1] | 2-(4'-methoxy-[1,1'-biphenyl]-3-yl)-N-(4-(5-methyl-2,4-dioxo-3,4-dihydro-pyrimidin-1(2H)-yl)phenyl)acetamide | C26H23N3O4 | 441 $R_t$ = 3.18 (441.49 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 32 | BB-7 + BB-13 | 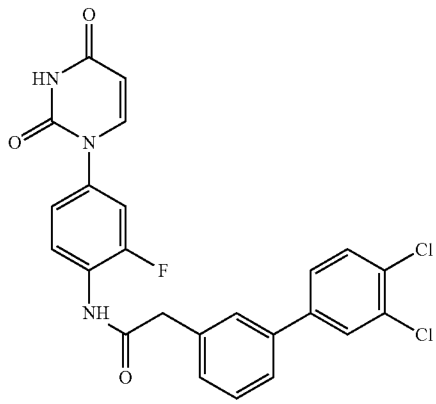 [SMILES: O=C(Cc1cccc(-c2ccc(Cl)c(Cl)c2)c1)Nc1ccc(-n2ccc(=O)[nH]c2=O)cc1F] | 2-(3',4'-dichloro-[1,1'-biphenyl]-3-yl)-N-(4-(2,4-dioxo-3,4-dihydro-pyrimidin-1(2H)-yl)-2-fluoro-phenyl)acetamide | C24H16Cl2FN3O3 | 486 $R_t$ = 3.28 (484.31 g/mol) |
| 33 | BB-2 + BB-16 | 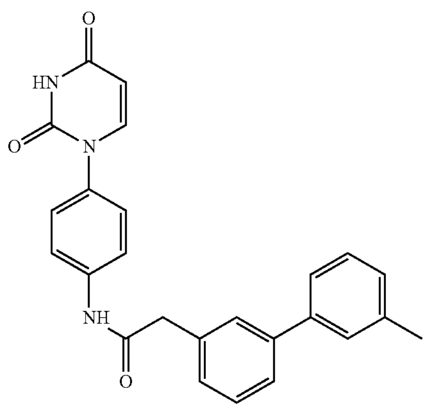 [SMILES: Cc1cccc(-c2cccc(CC(=O)Nc3ccc(-n4ccc(=O)[nH]c4=O)cc3)c2)c1] | N-(4-(2,4-dioxo-3,4-dihydro-pyrimidin-1(2H)-yl)phenyl)-2-(3'-methyl-[1,1'-biphenyl]-3-yl) acetamide | C25H21N3O3 | 411 $R_t$ = 3.02 (411.46 g/mol) |
| 34 | BB-9 + BB-30 | 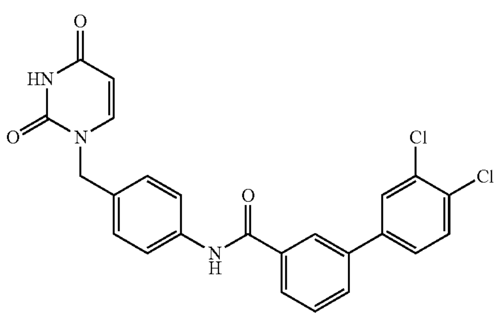 [SMILES: O=C(Nc1ccc(Cn2ccc(=O)[nH]c2=O)cc1)c1cccc(-c2ccc(Cl)c(Cl)c2)c1] | 3',4'-dichloro-N-(4-((2,4-dioxo-3,4-dihydro-pyrimidin-1(2H)-yl)methyl) phenyl)-[1,1'-biphenyl]-3-carboxamide | C24H17Cl2N3O3 | 466/468 $R_t$ = 3.35 (466.3 g/mol) |
| 35 | BB-9 + BB-29 | 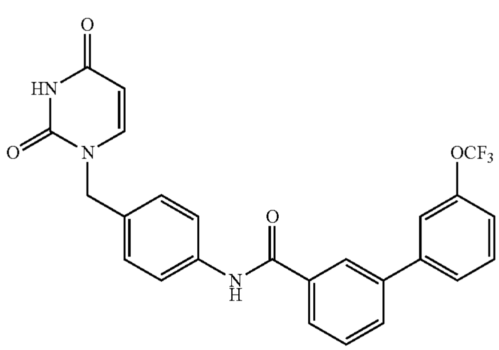 [SMILES: O=C(Nc1ccc(Cn2ccc(=O)[nH]c2=O)cc1)c1cccc(-c2cccc(OC(F)(F)F)c2)c1] | N-(4-((2,4-dioxo-3,4-dihydro-pyrimidin-1(2H)-yl)methyl) phenyl)-3'-(trifluoro-methoxy)-[1,1'-biphenyl]-3-carboxamide | C25H18F3N3O4 | 482 $R_t$ = 3.28 (481.43 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 36 | BB-9 + BB-25 | 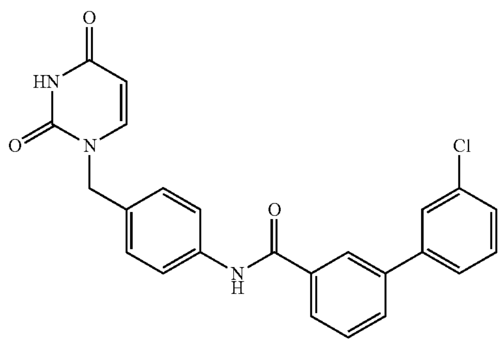 [SMILES: O=C(Nc1ccc(Cn2ccc(=O)[nH]c2=O)cc1)c1cccc(-c2cccc(Cl)c2)c1] | 3'-chloro-N-(4-((2,4-dioxo-3,4-dihydro-pyrimidin-1(2H)-yl)methyl)phenyl)-[1,1'-biphenyl]-3-carboxamide | C24H18ClN3O3 | 432/434 $R_t$ = 3.2 (431.9 g/mol) |
| 37 | BB-9 + BB-26 | 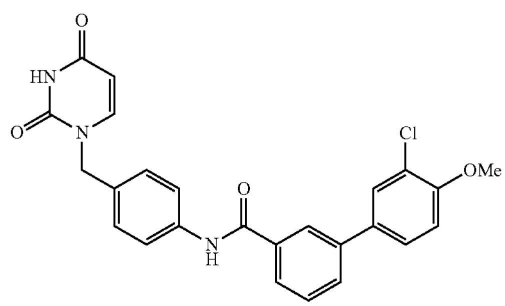 [SMILES: COc1ccc(-c2cccc(C(=O)Nc3ccc(Cn4ccc(=O)[nH]c4=O)cc3)c2)cc1Cl] | 3'-chloro-N-(4-((2,4-dioxo-3,4-dihydro-pyrimidin-1(2H)-yl)methyl)phenyl)-4'-methoxy-[1,1'-biphenyl]-3-carboxamide | C25H20ClN3O4 | 462/464 $R_t$ = 3.13 (461.9 g/mol) |
| 38 | BB-8 + BB-17 | 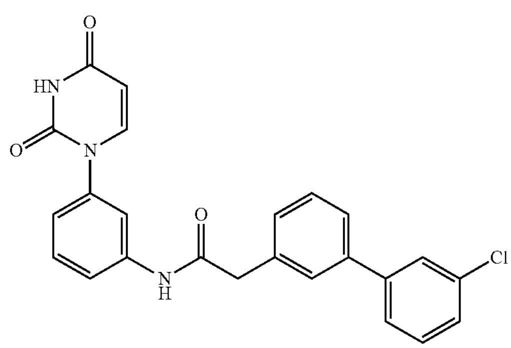 [SMILES: O=C(Cc1cccc(-c2cccc(Cl)c2)c1)Nc1cccc(-n2ccc(=O)[nH]c2=O)c1] | 3'-chloro-N-(4-((2,4-dioxo-3,4-dihydro-pyrimidin-1(2H)-yl)methyl)phenyl)-4'-methoxy-[1,1'-biphenyl]-3-carboxamide | C25H20ClN3O4 | 432/434 $R_t$ = 3.17 (431.9 g/mol) |
| 39 | BB-8 + BB-22 | 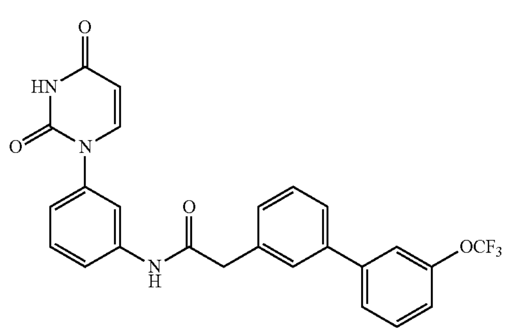 [SMILES: O=C(Cc1cccc(-c2cccc(OC(F)(F)F)c2)c1)Nc1cccc(-n2ccc(=O)[nH]c2=O)c1] | N-(3-(2,4-dioxo-3,4-dihydro-pyrimidin-1(2H)-yl)phenyl)-2-(3'-(trifluoro-methoxy)-[1,1'-biphenyl]-3-yl)acetamide | C25H18F3N3O4 | 468 $R_t$ = 3.28 (467.4 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 40 | BB-8 + BB-13 | 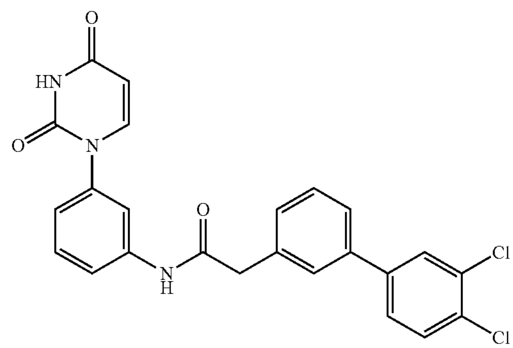 [SMILES: O=C(Cc1cccc(-c2ccc(Cl)c(Cl)c2)c1)Nc1cccc(-n2ccc(=O)[nH]c2=O)c1] | 2-(3',4'-dichloro-[1,1'-biphenyl]-3-yl)-N-(3-(2,4-dioxo-3,4-dihydro-pyrimidin-1(2H)-yl)phenyl)acetamide | C24H17Cl2N3O3 | 466/468 R$_t$ = 3.33 (466.3 g/mol) |
| 41 | BB-8 + BB-18 | 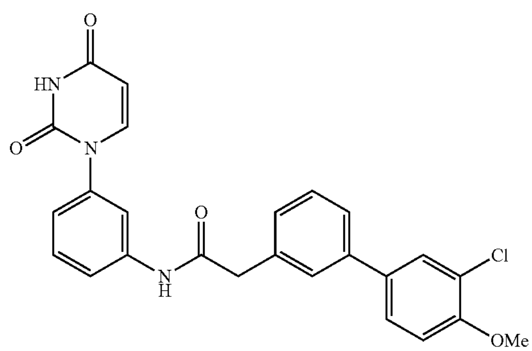 [SMILES: COc1ccc(-c2cccc(CC(=O)Nc3cccc(-n4ccc(=O)[nH]c4=O)c3)c2)cc1Cl] | 2-(3'-chloro-4'-methoxy-[1,1'-biphenyl]-3-yl)-N-(3-(2,4-dioxo-3,4-dihydro-pyrimidin-1(2H)-yl)phenyl)acetamide | C25H20ClN3O4 | 462/464 R$_t$ = 3.1 (461.9 g/mol) |
| 42 | BB-2 + BB-24 | 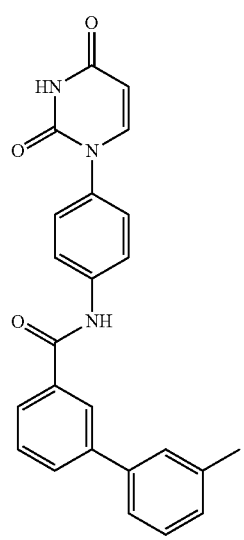 [SMILES: Cc1cccc(-c2cccc(C(=O)Nc3ccc(-n4ccc(=O)[nH]c4=O)cc3)c2)c1] | N-(4-(2,4-dioxo-3,4-dihydro-pyrimidin-1(2H)-yl)phenyl)-3'-methyl-[1,1'-biphenyl]-3-carboxamide | C24H19N3O3 | 398 R$_t$ = 3.08 (397.43 g/mol) |

TABLE 5-continued

Further compounds prepared (according to synthesis of compound 1)

| No | Structure | Name | Molecular formula | MS(ESI) m/z (M + H)+ (Calc Mass) |
|----|-----------|------|-------------------|----------------------------------|
| 43 | BB-2 + BB-25 | 3'-chloro-N-(4-(2,4-dioxo-3,4-dihydro-pyrimidin-1(2H)-yl)phenyl)-[1,1'-biphenyl]-3-carboxamide | C23H16ClN3O3 | 418 $R_t$ = 3.1 (417.85 g/mol) |
| 44 | BB-2 + BB-26 | 3'-chloro-N-(4-(2,4-dioxo-3,4-dihydro-pyrimidin-1(2H)-yl)phenyl)-4'-methoxy-[1,1'-biphenyl]-3-carboxamide | C24H18ClN3O4 | 448 $R_t$ = 3.03 (447.88 g/mol) |

TABLE 5-continued

| | | Further compounds prepared (according to synthesis of compound 1) | | |
|---|---|---|---|---|
| No | Structure | Name | Molecular formula | MS(ESI) m/z $(M + H)^+$ (Calc Mass) |
| 45 | BB-1 + BB-26 | 3'-chloro-4'-methoxy-N-(4-(5-methyl-2,4-dioxo-3,4-dihydro-pyrimidin-1(2H)-yl)phenyl)-[1,1'-biphenyl]-3-carboxamide | C25H20ClN3O4 | 462 $R_t$ = 3.02 (461.9 g/mol) |
| 46 | BB-1 + BB-23 | 3'-methoxy-N-(4-(5-methyl-2,4-dioxo-3,4-dihydro-pyrimidin-1(2H)-yl)phenyl)-[1,1'-biphenyl]-3-carboxamide | C25H21N3O4 | 428 $R_t$ = 3.02 (427.66 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 47 | BB-1 + BB-29 | 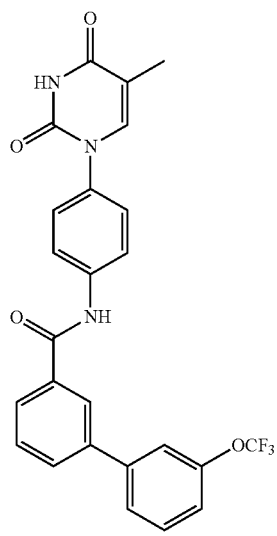 [SMILES: Cc1cn(-c2ccc(NC(=O)c3cccc(-c4cccc(OC(F)(F)F)c4)c3)cc2)c(=O)[nH]c1=O] | N-(4-(5-methyl-2,4-dioxo-3,4-dihydro-pyrimidin-1(2H)-yl)phenyl)-3'-(trifluoro-methoxy)-[1,1'-biphenyl]-3-carboxamide | C25H18F3N3O4 | 482 $R_t$ = 3.30 (481.43 g/mol) |
| 48 | BB-4 + BB-29 | 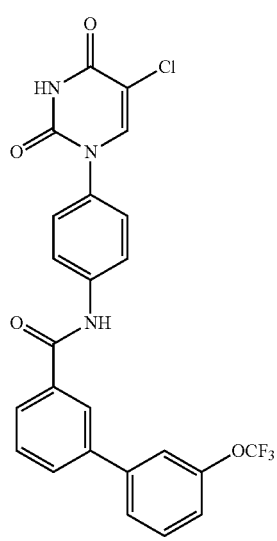 | N-(4-(5-chloro-2,4-dioxo-3,4-dihydro-pyrimidin-1(2H)-yl)phenyl)-3'-(trifluoro-methoxy)-[1,1'-biphenyl]-3-carboxamide | C24H15ClF3N3O4 | 502 $R_t$ = 3.4 (501.85 g/mol) |

TABLE 5-continued

Further compounds prepared (according to synthesis of compound 1)

| No | | Structure | Name | Molecular formula | MS(ESI) m/z (M + H)+ (Calc Mass) |
|---|---|---|---|---|---|
| 49 | BB-1 + BB-28 | | 3'-chloro-4'-methyl-N-(4-(5-methyl-2,4-dioxo-3,4-dihydro-pyrimidin-1(2H)-yl)phenyl)-[1,1'-biphenyl]-3-carboxamide | C25H20ClN3O3 | 446 $R_t$ = 3.38 (445.9 g/mol) |
| 50 | BB-2 + BB-28 | | 3'-chloro-N-(4-(2,4-dioxo-3,4-dihydro-pyrimidin-1(2H)-yl)phenyl)-4'-methyl-[1,1'-biphenyl]-3-carboxamide | C24H18ClN3O3 | 432 $R_t$ = 3.35 (431.8 g/mol) |
| 51 | BB-4 + BB-13 | | N-(4-(5-chloro-2,4-dioxo-3,4-dihydro-pyrimidin-1(2H)-yl)phenyl)-2-(3',4'-dichloro-[1,1'-biphenyl]-3-yl)acetamide | C24H16Cl3N3O3 | 500/502 $R_t$ = 3.43 (500.76 g/mol) |

Compound 52: N-(3,4-dichlorophenyl)-2-(1-(4-(2,4-dioxo-3,4-dihydropyrimidin-1(2H)-yl)phenyl)-1H-1,2,3-triazol-4-yl)acetamide

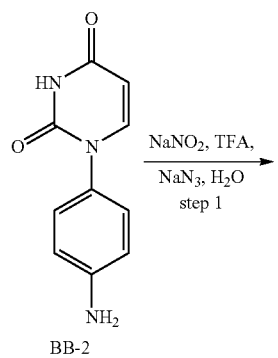

BB-2

NaNO₂, TFA,
NaN₃, H₂O
step 1

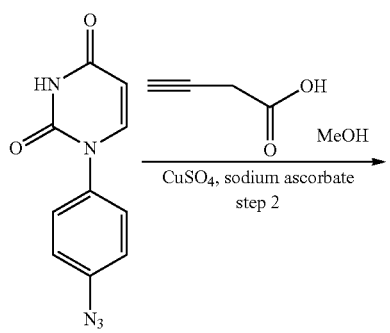

MeOH
CuSO₄, sodium ascorbate
step 2

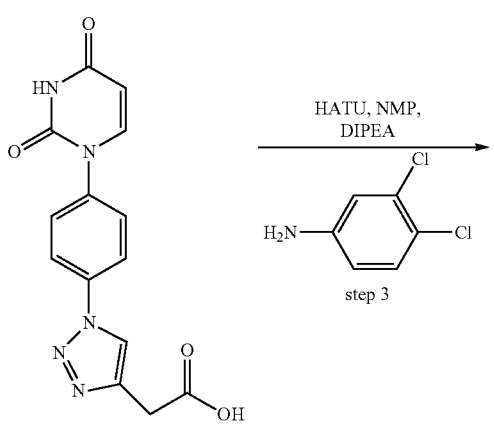

HATU, NMP,
DIPEA
step 3

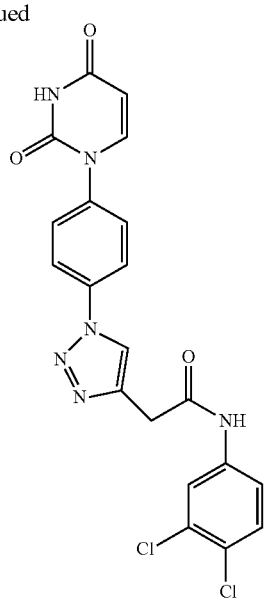

Step 1: 1-(4-Azidophenyl)pyrimidine-2,4(1H,3H)-dione

To a solution of BB-2 (100 mg) in TFA (3 ml) is added at 0° C. sodium nitrite in small portions (29 mg). The mixture is stirred at 0° C. for 30 min. Afterwards a solution of sodium azide (79.2 mg) in water (0.6 ml) is added. The mixture is stirred at 0° C. and allowed to warm to room temperature. Water and ethyl acetate are added. The water phase is extracted two times with ethyl acetate. The organic layers are dried (Na₂SO₄) then concentrated in vacuum to give the desired product.

(C10H7N5O2) Mass calc. 229.2 g/mol, (ESI) m/z: 230. The compound is used without further purification in the next step.

Step 2: 2-(1-(4-(2,4-Dioxo-3,4-dihydropyrimidin-1(2H)-yl)phenyl)-1H-1,2,3-triazol-4-yl)acetic acid To a solution of 1-(4-azidophenyl)pyrimidine-2,4(1H,3H)-dione (100 mg) in methanol (2.2 ml) butynoic acid (37 mg) is added. To this mixture a CuSO₄ solution (0.218 ml) and a sodium ascorbate solution (0.218 ml) are added. Both solutions were prepared before on ice: 25 mg CuSO₄*5 H₂O in 0.5 ml H₂O and 35 mg sodium ascorbate in 0.5 ml H₂O.

The mixture is stirred over night at 60° C. After cooling down, water and ethyl acetate are added. After extraction the water phase is acidified and extracted two times with ethyl acetate. The organic layers are dried (Na₂SO₄) then concentrated in vacuum to give the desired product.

Mass calc. 313.37 g/mol, (ESI) (M+H)⁺ m/z: 314. The compound is used without further purification in the next step.

Step 3: N-(3,4-Dichlorophenyl)-2-(1-(4-(2,4-dioxo-3,4-dihydropyrimidin-1(2H)-yl)phenyl)-1H-1,2,3-triazol-4-yl)acetamide To a solution of 2-(1-(4-(2,4-dioxo-3,4-dihydropyrimidin-1(2H)-yl)phenyl)-1H-1,2,3-triazol-4-yl)acetic acid (68.9 mg), HATU (96.9 mg) in NMP (990 μl) were added 3,4-dichloro aniline (16.1 mg) and DIPEA (38.2 μl). The reaction mixture is stirred over night at room temperature. Ethyl acetate is added and washed with water. The organic layers are dried (Na$_2$SO$_4$) then concentrated in vacuum. The residue is purified by normal phase chromatography (CH$_2$Cl$_2$: MeOH:Et$_3$N (20:1:0.1)). The fractions containing the product are evaporated to yield a white solid.

(C$_{20}$H$_{14}$Cl$_2$N$_6$O$_3$) Mass calc. 457.3 g/mol; Rt=2.90 min; MS (ESI) m/z: 457/459 (M+H)$^+$.

Compound 53: N-benzyl-2-(1-(4-(2,4-dioxo-3,4-dihydropyrimidin-1(2H)-yl)phenyl)-1H-1,2,3-triazol-4-yl)acetamide

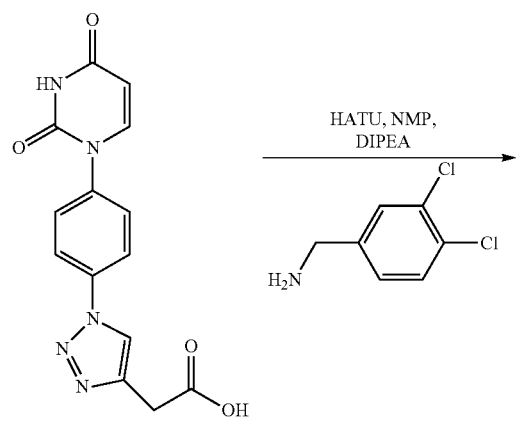

Compound 53 was synthesized following a similar procedure as described for compound 52 (step 3) using 3,4-dichlorobenzyl amine.

(C$_{21}$H$_{16}$N$_6$O$_3$) Mass calc. 471.3 g/mol Rt=2.77 min; MS (ESI) m/z: 471/473 (M+H)$^+$.

Compound 54: 3,4-Dichloro-N-((1-(4-(2,4-dioxo-3,4-dihydropyrimidin-1(2H)-yl)phenyl)-1H-1,2,3-triazol-4-yl)methyl)benzamide

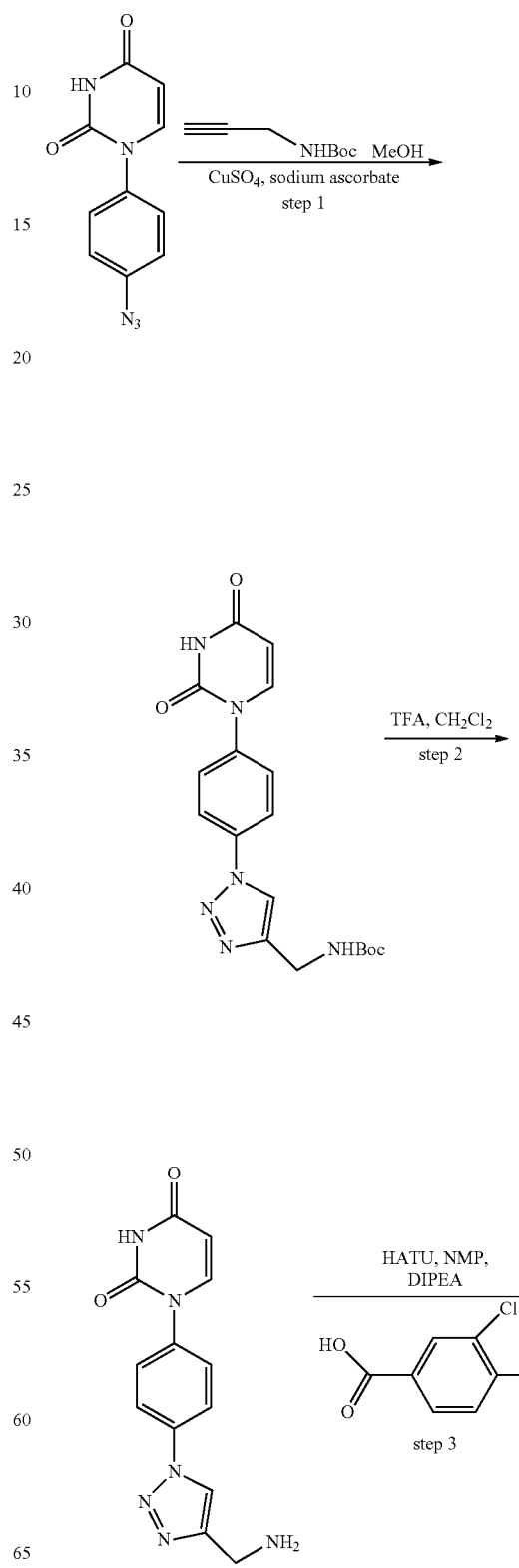

85

-continued

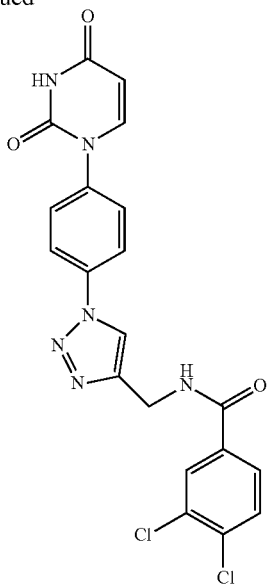

Step 1: Tert-butyl ((1-(4-(2,4-dioxo-3,4-dihydropyrimidin-1(2H)-yl)phenyl)-1H-1,2,3-triazol-4-yl)methyl)carbamate To a solution of 1-(4-azidophenyl)pyrimidine-2,4(1H,3H)-dione (50 mg) in methanol (545 μl) is added N-boc-propargylamine (33.6 mg). To this mixture a CuSO$_4$ solution (54.5 μl) and a sodium ascorbate solution (54.5 μl) are added. Both solutions were prepared before on ice: 25 mg CuSO$_4$*5 H$_2$O in 0.5 ml H$_2$O and 35 mg sodium ascorbate in 0.5 ml H$_2$O.

The mixture is stirred over night at 60° C. After cooling down, water and ethyl acetate are added. The water phase is extracted two times with ethyl acetate. The organic layers are dried (Na$_2$SO$_4$) then concentrated in vacuum to give the desired product. (C$_{18}$H$_{20}$N$_6$O$_4$) Mass calc. 384.4 g/mol, (ESI) (M+H-boc)$^+$ m/z: 286. The compound is used without further purification in the next step.

Step 2: 1-(4-(4-(Aminomethyl)-1H-1,2,3-triazol-1-yl)phenyl)pyrimidine-2,4(1H,3H)-dione To a solution of tert-butyl ((1-(4-(2,4-dioxo-3,4-dihydropyrimidin-1(2H)-yl)phenyl)-1H-1,2,3-triazol-4-yl)methyl)carbamate (18 mg) in dichloromethane (3 ml) is added TFA (1.5 ml). The mixture is stirred for 2 h. Afterwards the solvent is evaporated to give the desired product.

(C$_{13}$H$_{12}$N$_6$O$_2$) Mass calc. 284.4 g/mol, (ESI) (M+H)$^+$ m/z: 285. The compound is used without further purification in the next step.

Step 3: 3,4-Dichloro-N-((1-(4-(2,4-dioxo-3,4-dihydropyrimidin-1(2H)-yl)phenyl)-1H-1,2,3-triazol-4-yl)methyl)benzamide Step 3 following a similar procedure as described for compound 51 (step 3).

(C$_{20}$H$_{14}$Cl$_2$N$_6$O$_3$), Mass calc. 457.3 g/mol, Rt=2.90, (ESI) (M+H)$^+$ m/z: 457/459.

86

Compound 55: 2-(3,4-Dichlorophenyl)-N-((1-(4-(2,4-dioxo-3,4-dihydropyrimidin-1(2H)-yl)phenyl)-1H-1,2,3-triazol-4-yl)methyl)acetamide

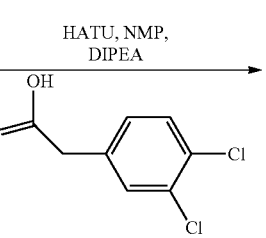

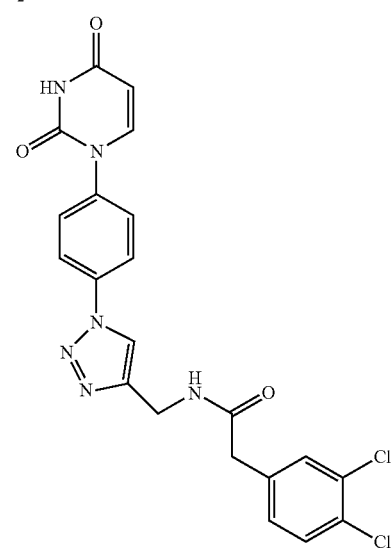

Compound 55 was synthesized following a similar procedure as described for compound 54 (step 3) using 3,4-dichlorobenzyl amine.

(C$_{21}$H$_{16}$Cl$_2$N$_6$O$_3$) Mass calc. 471.3 g/mol, Rt=2.72, (ESI) (M+H)$^+$ m/z: 471/473.

Compound 56: 1-(4-(4-(3,4-Dichlorophenyl)-1H-1,2,3-triazol-1-yl)phenyl)pyrimidine-2,4(1H,3H)-dione

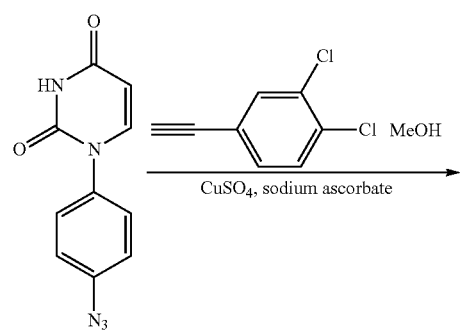

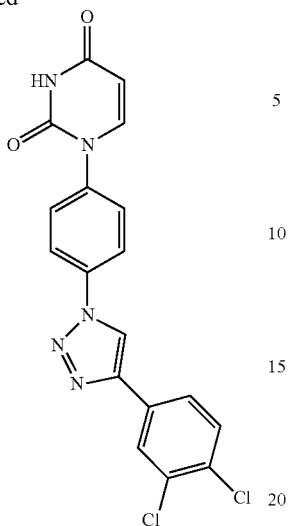

Compound 56 was synthesized following a similar procedure as described for compound 54 (step 1) using 3,4-dichlorophenyl acetylene.

($C_{18}H_{11}Cl_2N_5O_2$) Mass calc. 400.2 g/mol, Rt=3.18, (ESI) (M+H)+ m/z: 400/402.

Aggregation Assay:

Description of Aggregation Assay Method:

To test how small molecules affect the chaperone activity of HSP27, misfolding and aggregation of citrate synthase (CS), a well-known in vitro client protein of HSP27, was measured. Citrate synthase misfolds and aggregates when exposed to heat shock at 43° C. This heat denaturation is prevented or delayed in the presence of HSP27 (CS+HSP27) (Jakob et al. (1993)). To determine the influence of test compounds according to the invention on the chaperone activity of HSP27, CS was denaturated at 43° C. using 1.44 µM CS, 481 nM HSP27 in a 40 mM HEPES buffer (pH 7.4) in the presence or absence of test compound. The samples were incubated at 43° C. and the aggregation behavior of CS was monitored in a spectrometer (PerkinElmer LS55) at a wavelength of 500 nm. Substances inhibiting HSP27's chaperone activity lead to continued denaturation of the client protein and its aggregation in solution. This inhibition correlates with the strength of the interaction between HSP27 and the test substance, which is related to its binding efficiency.

In the reference experiment BVDU (CS+HSP27+BVDU) was tested at a concentration of 750 µM as previously described (Heinrich et al. (2016)).

The compounds according to the invention were tested at a concentration of 10 µM.

Table 6 shows the HSP27 inhibition values for compounds according to the invention.

Results Aggregation Assay:

TABLE 6

Results of aggregation assay showing number of compound used (in a mixture of CS + HSP27) and aggregation value related to the value from reference experiment (CS + HSP27 + BVDU), which was set at 1.0.

| | |
|---|---|
| 1 | 1.76 |
| 2 | 1.55 |
| 3 | 1.44 |
| 4 | 1.39 |
| 5 | 1.39 |
| 6 | 1.38 |
| 7 | 1.35 |
| 8 | 1.34 |
| 9 | 1.3 |
| 10 | 1.3 |
| 11 | 1.28 |
| 12 | 1.57 |
| 13 | 1.21 |
| 14 | 1.2 |
| 15 | 1.11 |
| 16 | 1.04 |
| 17 | 1.01 |
| 18 | 1 |
| 19 | 0.97 |
| 20 | 0.96 |
| 21 | 0.94 |
| 22 | 0.91 |
| 23 | 1.33 |
| 24 | 0.88 |
| 25 | 0.88 |
| 26 | 0.85 |
| 27 | 0.83 |
| 28 | 0.82 |
| 29 | 0.8 |
| 30 | 0.79 |
| 31 | 0.78 |
| 32 | 0.76 |
| 33 | 0.69 |
| 34 | 1.8 |
| 35 | 1.55 |
| 36 | 1.23 |
| 37 | 0.91 |
| 38 | 1.19 |
| 39 | 1.21 |
| 40 | 1.8 |
| 41 | 1.24 |
| 42 | 0.66 |
| 43 | 0.79 |
| 44 | 0.83 |
| 45 | 0.88 |
| 46 | 0.75 |
| 47 | 1.46 |
| 48 | 0.7 |
| 49 | 1.16 |
| 50 | 0.73 |
| 51 | 0.73 |
| 52 | 1 |
| 53 | 1.67 |
| 54 | 1.42 |
| 55 | 1.05 |
| 56 | 1.39 |

Comparative Examples

TABLE 7

Results of aggregation assay showing known compounds used (in a mixture of CS + HSP27) and aggregation value related to the value from reference experiment (CS + HSP27 + BVDU)

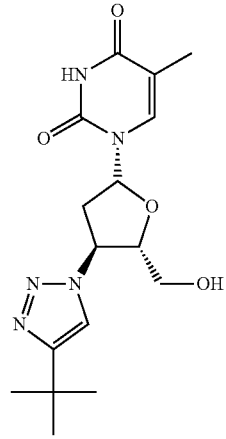

0.61

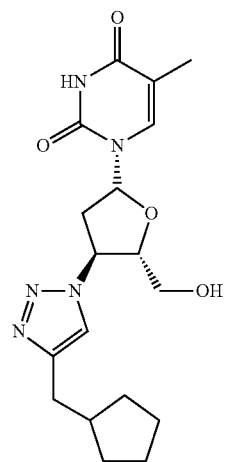

0.66

TABLE 7-continued

Results of aggregation assay showing known compounds used (in a mixture of CS + HSP27) and aggregation value related to the value from reference experiment (CS + HSP27 + BVDU)

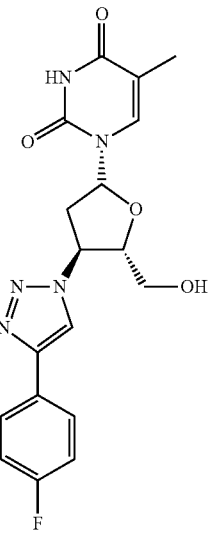

0.66

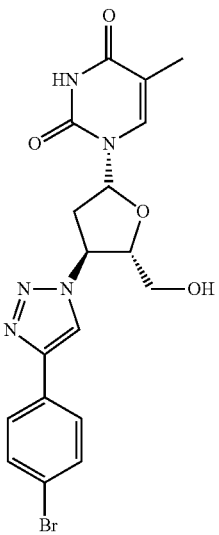

0.64

TABLE 7-continued

Results of aggregation assay showing known compounds used (in a mixture of CS + HSP27) and aggregation value related to the value from reference experiment (CS + HSP27 + BVDU)

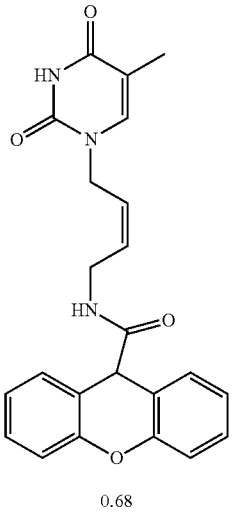

0.68

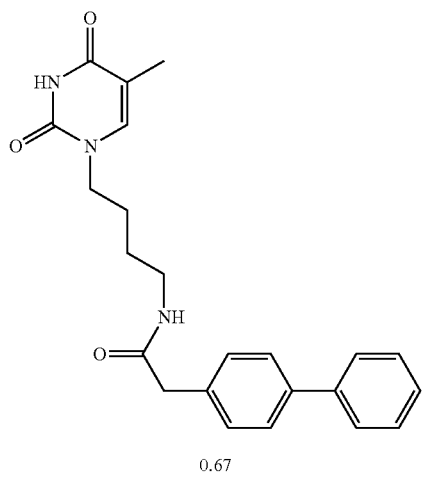

0.67

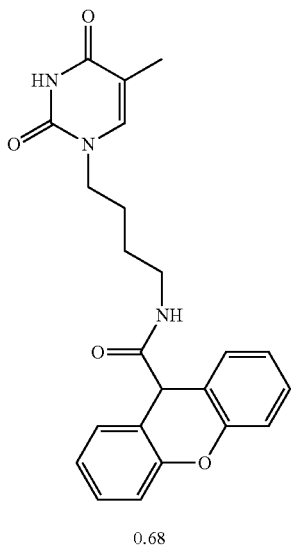

0.68

TABLE 7-continued

Results of aggregation assay showing known compounds used (in a mixture of CS + HSP27) and aggregation value related to the value from reference experiment (CS + HSP27 + BVDU)

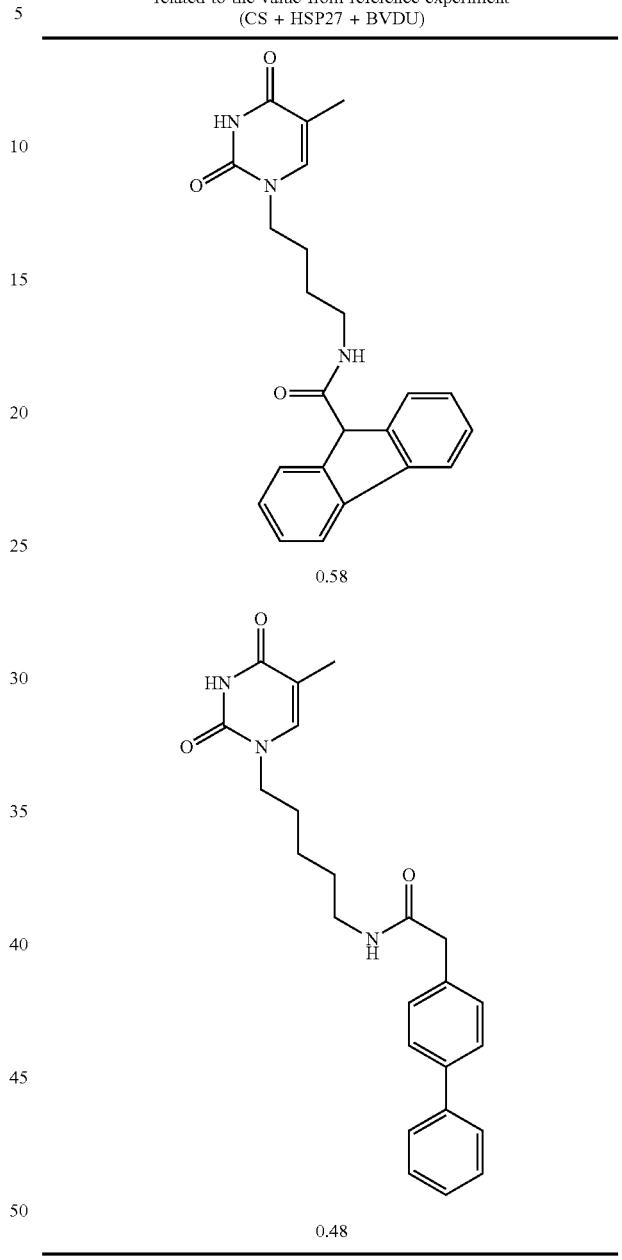

0.58

0.48

Chemoresistance Assay:
Description of Chemoresistance Assay Method:

In a chemoresistance assay, a HSP27 dependent resistance to a cytostatic drug is induced in cultured cells by slowly increasing the dose of the cytostatic over several cell passages. This approach is valid for multiple cell types and cytostatic drugs and allowed us to test compounds according to the invention for their ability to inhibit HSP27 and reestablish susceptibility of the resistant cells to the cancer drug.

RPM-8226 cells, a human multiple myeloma cell line, were obtained from DSMZ (Leibniz Institute DSMZ-German Collection of Microorganisms and Cell Cultures). Cells were grown in RPMI 1640 medium (FG 1235; Biochrom AG, Berlin, Germany) supplemented with 10% (v/v) heatinactivated fetal bovine serum in a humidified atmosphere containing 5% $CO_2$ at 37° C. Logarithmically growing cells were seeded at a density of 100,000 cells/ml and incubated with Bortezomib (Velcade) in combination with or without test compounds. Cells were periodically counted using C-Chip Neubauer-improved counting chambers (Peqlab) and serially passaged. Cells were maintained below 1,000,000 cells/ml and typically passaged when the cell count reached 800,000 cells/ml. The starting dose of Bortezomib was typically 0.1 ng/ml and the concentration of Bortezomib was increased with each passage, e.g.: 1st passage, 0.1 ng/ml Bortezomib, 2nd passage 0.2 ng/ml Bortezomib, 3rd passage 0.3 ng/ml Bortezomib, etc.

Over 3-4 passages with increasing concentration of Bortezomib, cells begin to show resistance and finally grow at the same rate as untreated cells.

The addition of HSP27 inhibitors prevents development of chemoresistance and reestablishes the killing effect of Bortezomib. Cell numbers are determined at the end of the final passage to compare their growth rates.

As a reference compound, BVDU was tested at a concentration of 30 µM as previously described (Heinrich et al. (2016)). The compounds according to the invention were tested at a concentration of 1 µM or lower (see below). Test compounds were added at the start of the experiment and again after each passage and their concentrations remained unchanged throughout. Untreated cells, and cells treated with only BVDU or test compound served as controls did not influence cell growth. The appropriate non-toxic dose of the test compound was determined in a dose-finding experiment beforehand.

Results Chemoresistance Assay:

FIG. 1a: Results of chemoresistance assay showing the resensitization of chemoresistant RPMI 8226 multiple myeloma cells to Bortezomib after treatment with test compounds. RPMI-8226 cells (100,000) were seeded and cultured in the presence of rising concentrations of Bortezomib (0.5-1 nM or 0.75-1.3 nM) and HSP27 inhibitor, and passaged every 4-7 days. Cell counts were taken after the last passage at the highest concentration of Bortezomib and relative cell number determined. Test compounds were BVDU, and Compound 12 and Compound 4, according to the invention.

FIG. 1b: Results of chemoresistance assay showing the resensitization of chemoresistant 2950-K9 mouse colon carcinoma cells to the drug 5-Fluorouracil (5-FU) after treatment with test compounds. 2950-K9 cells (100,000) were seeded and cultured in the presence of rising concentrations of 5-FU (12-20 nM) and HSP27 inhibitor, and passaged every 4-7 days. Cell counts were taken after the last passage at the highest concentration of 5-FU and relative cell number determined. Test compounds were BVDU, and Compound 5, Compound 12 and Compound 4, according to the invention.

NON-PATENT LITERATURE

Heinrich J. C.; Donakonda, S.; Haupt, V. J.; Lennig, P.; Zhang, Y.; Schroeder, M. *New HSP27 inhibitors efficiently suppress drug resistance development in cancer cells* Oncotarget 2016, 7, 68156-68169.

Hernández, A-I.; Balzarini, J.; Rodríguez-Barrios, F.; San-Felix, A.; Karlsson, A.; Gago, F.; Camarasa, M.-J.; Pérez-Pérez, M. J. *Improving the Selectivity of Acyclic Nucleoside Analogues as Inhibitors of Human Mitochondrial Thymidine Kinase: Replacement of a Triphenylmethoxy Moiety with Substituted Amines and Carboxyamides* Bioorganic & Medicinal Chemistry Letters 2003, 13, 3027-3030.

Hildebrand, C.; Sandoli, D.; Focher, F.; Gambino, J.; Ciarrocchi, G.; Spadari, S.; Wright, G. *Structure-Activity Relationships of $N^2$-Substituted Guanines as Inhibitors of HSV1 and HSV2 Thymidine Kinases* J. Med. Chem. 1990, 33, 203-206.

Jakob, U.; Gaestel, M.; Engel, K.; Buchner, J. *Small heat shock proteins are molecular chaperones* J. Biol. Chem. 1993, 268, 1517-1520.

The invention claimed is:

1. A compound according to general formula (I), or a salt or prodrug thereof:

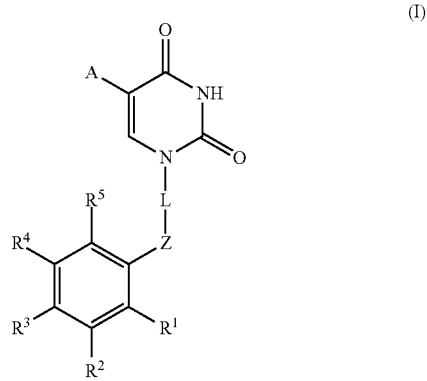

wherein substituent A is —H, -Hal, -Me or —$CF_3$, linker L is an aromat selected from a para- or meta-linked phenyl or benzyl group, both substituted or unsubstituted, wherein the $CH_2$ of the benzyl group is arranged in a direction, that it binds to the nitrogen in general formula (I), and wherein Z is selected from:

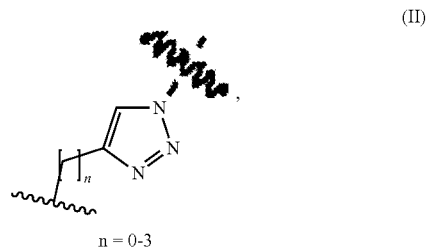

n = 0-3

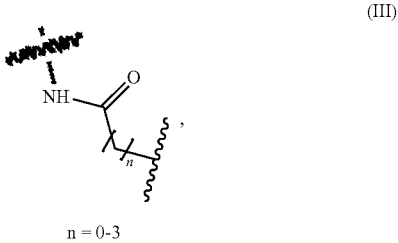

n = 0-3

-continued

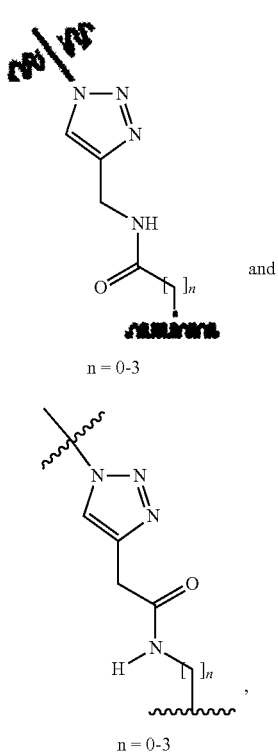

wherein the nitrogen in formulas (II), (III), (IV) and (V) binds to L, and
wherein
substituents $R^1$, $R^3$, $R^4$ and $R^5$ are independently selected from —H, -Hal, —$CF_3$, -Me, —OMe, —$OCF_3$ and —$O^iPr$, OEt, and substituent $R^2$ is selected from substituted phenyl, unsubstituted phenyl, —H, -Hal, —$CF_3$, -Me, —OMe, —$OCF_3$, —$O^iPr$ and OEt.

2. The compound, or salt or prodrug according to claim 1, wherein linker L is substituted at the aromat with alkyl, methoxy and/or halogen.

3. A method of inhibiting HSP27 in a subject, said method comprising administering to the subject the compound, or salt or prodrug thereof according to claim 1.

4. A method for treating carinoma, a HSP27 associated disease, or cystic fibrosis, said method comprising administering to a subject in need thereof a therapeutically effective amount of the compound, or salt or prodrugs thereof according to claim 1.

5. The method according to claim 4, for treating carcinoma, wherein the compound, or salt or prodrug thereof is used in combination with chemotherapy, radiotherapy and/or cancer immunotherapy.

6. The method according to claim 5, wherein
the compound, or salt or prodrug thereof is administered before starting chemotherapy, radiotherapy and/or cancer immunotherapy and
administration of the compound or salt or prodrug thereof is continued during the chemotherapy, radiotherapy and/or cancer immunotherapy to suppress development of resistances.

7. A pharmaceutical product containing the compound, or salt or prodrug thereof according to claim 1.

8. The pharmaceutical product according to claim 7 additionally comprising at least one further active ingredient.

9. The pharmaceutical product according to claim 8, wherein the further active ingredient is selected from cancerostatic agents, alkylating agents, inhibitors of DNA replication, inhibitors of DNA transcription and angionesis inhibitors.

* * * * *